(12) United States Patent
Bushby

(10) Patent No.: US 12,186,219 B2
(45) Date of Patent: *Jan. 7, 2025

(54) THERAPEUTIC ARTICLE OF MANUFACTURE FOR ADHESIVE APPLICATION TO THE SKIN OF A USER

(71) Applicant: Applied BioKinetics LLC, Spring, TX (US)

(72) Inventor: Donald P. Bushby, Spring, TX (US)

(73) Assignee: Applied BioKinetics LLC, American Fork, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/420,354

(22) Filed: Jan. 23, 2024

(65) Prior Publication Data
US 2024/0197513 A1 Jun. 20, 2024

Related U.S. Application Data

(63) Continuation of application No. 18/334,372, filed on Jun. 13, 2023, which is a continuation of application
(Continued)

(51) Int. Cl.
*A43B 7/14* (2022.01)
*A43B 7/1405* (2022.01)
(Continued)

(52) U.S. Cl.
CPC ............ *A61F 5/0111* (2013.01); *A43B 7/141* (2013.01); *A43B 7/142* (2013.01); *A43B 7/1425* (2013.01);
(Continued)

(58) Field of Classification Search
CPC ........ A61F 5/01; A61F 5/0111; A61F 13/067; A61F 2013/00246; A61F 2013/0091;
(Continued)

(56) References Cited

U.S. PATENT DOCUMENTS

| | | | |
|---|---|---|---|
| 8,216,162 B2 * | 7/2012 | Bushby | A61F 5/0127 602/61 |
| 8,414,511 B2 * | 4/2013 | Bushby | A43B 7/145 602/61 |

(Continued)

OTHER PUBLICATIONS

"Arch Taping Technique No. 3," 2 pages.
(Continued)

*Primary Examiner* — Tarla R Patel
(74) *Attorney, Agent, or Firm* — Dentons Durham Jones Pinegar; Sarah W. Matthews; Lilly Godfrey

(57) ABSTRACT

A therapeutic article of manufacture suitable for adhesive application to the skin of a user includes an elongate support layer formed of a single layer of woven fabric. The woven fabric has a ratio of elongation in percent to tensile strength (lb/in-width) that is less than 0.9 in only one of two test directions, where elongation, tensile strength, and test directions are determined under test conditions specified in ASTM (American Society for Testing and Materials) D3759. The article of manufacture additionally includes an adhesive intermittent across the support layer and a removable cover layer releasably retained on the adhesive.

12 Claims, 27 Drawing Sheets

Related U.S. Application Data

No. 17/384,503, filed on Jul. 23, 2021, now Pat. No. 11,690,746, which is a continuation of application No. 16/387,250, filed on Apr. 17, 2019, now Pat. No. 11,096,815, which is a continuation of application No. 15/240,783, filed on Aug. 18, 2016, now Pat. No. 10,299,953, which is a continuation of application No. 13/783,632, filed on Mar. 4, 2013, now Pat. No. 10,212,987, which is a continuation of application No. 13/477,015, filed on May 21, 2012, now Pat. No. 8,834,397, which is a continuation of application No. 11/165,304, filed on Jun. 23, 2005, now Pat. No. 8,216,162, and a continuation-in-part of application No. 10/817,172, filed on Apr. 2, 2004, now Pat. No. 8,414,511.

(51) Int. Cl.

| | | |
|---|---|---|
| *A43B 7/142* | (2022.01) | |
| *A43B 7/1425* | (2022.01) | |
| *A43B 7/143* | (2022.01) | |
| *A43B 7/1435* | (2022.01) | |
| *A43B 7/144* | (2022.01) | |
| *A43B 7/1445* | (2022.01) | |
| *A43B 7/145* | (2022.01) | |
| *A43B 13/34* | (2006.01) | |
| *A61F 5/00* | (2006.01) | |
| *A61F 5/01* | (2006.01) | |
| *A61F 13/00* | (2024.01) | |
| *A61F 13/06* | (2006.01) | |
| *B29D 11/00* | (2006.01) | |
| *B32B 3/02* | (2006.01) | |
| *B32B 3/26* | (2006.01) | |
| *B32B 5/02* | (2006.01) | |
| *B32B 7/06* | (2019.01) | |
| *B32B 7/12* | (2006.01) | |
| *B32B 27/06* | (2006.01) | |

(52) U.S. Cl.
CPC ............ *A43B 7/143* (2013.01); *A43B 7/1435* (2013.01); *A43B 7/144* (2013.01); *A43B 7/1445* (2013.01); *A43B 7/145* (2013.01); *A43B 7/1495* (2013.01); *A61F 13/067* (2013.01); *B32B 3/02* (2013.01); *B32B 3/266* (2013.01); *B32B 5/022* (2013.01); *B32B 5/024* (2013.01); *B32B 7/06* (2013.01); *B32B 7/12* (2013.01); *B32B 27/06* (2013.01); *A61F 2013/00246* (2013.01); *A61F 2013/00272* (2013.01); *A61F 2013/0028* (2013.01); *A61F 2013/0091* (2013.01); *B32B 2255/02* (2013.01); *B32B 2262/04* (2013.01); *B32B 2307/54* (2013.01); *B32B 2307/724* (2013.01); *B32B 2307/732* (2013.01); *B32B 2307/744* (2013.01); *B32B 2307/748* (2013.01); *B32B 2405/00* (2013.01); *B32B 2535/00* (2013.01)

(58) Field of Classification Search
CPC ... A61F 2013/0028; A61F 2013/00272; A43B 7/14; A43B 23/02; A43B 21/24; A43B 7/28; A43B 7/143; A43B 7/142; A43B 7/1445; A43B 7/145; A43B 7/1425; A43B 7/144; A43B 7/1495; A43B 7/141; A43B 7/1435; B32B 5/022; B32B 5/024; B32B 7/06; B32B 7/12; B32B 27/06; B32B 3/02; B32B 3/266; B32B 2262/04; B32B 2255/02; B32B 2307/724; B32B 2307/732; B32B 2307/744; B32B 2307/748; B32B 2405/00; B32B 2535/00; B32B 2307/54

USPC ....... 602/1, 28, 29; 36/140, 43, 44; 706/924, 706/932, 934; 704/270; 206/363, 438, 206/440, 441, 828; 423/108–118

See application file for complete search history.

(56) References Cited

U.S. PATENT DOCUMENTS

| | | | |
|---|---|---|---|
| 8,814,818 B2 * | 8/2014 | Bushby | A61F 5/0111 523/108 |
| 8,834,397 B2 * | 9/2014 | Bushby | B65B 5/10 523/108 |
| 10,212,987 B2 * | 2/2019 | Bushby | B26D 7/32 |
| 10,299,953 B2 * | 5/2019 | Bushby | A43B 7/1435 |
| 11,096,815 B2 * | 8/2021 | Bushby | B32B 5/022 |
| 11,206,894 B2 * | 12/2021 | Bushby | B26D 3/10 |
| 11,690,746 B2 * | 7/2023 | Bushby | A43B 7/1445 602/23 |

OTHER PUBLICATIONS

Clinical Therapeutics, 3 pages.
Hoey et al., "Foot morphological variations between different ethnicities and sex: a systemic review," Footwear Science, Dec. 15, 2022, 18 pages.
Illustrated Taping Techniques, 2 pages.
Isvilanonda et al., "Regional differences in the mechanical properties of the plantar aponeurosis," Journal of Biomechanics 151 (2023), 7 pages.
Saxelby, et al., "'Low-Dye' taping on the foot in the management of plantar-fasciitis," The Foot, 1997, 5 pages.
Zhang et al., "Anatomical features of plantar fasciitis in various age cohorts: Based on magnetic resonance imaging," Journal of Orthopaedic Surgery 31(1) , 2023, 7 pages.

* cited by examiner

THERAPEUTIC ARTICLE OF MANUFACTURE FOR ADHESIVE APPLICATION TO THE SKIN OF A USER

BACKGROUND OF THE INVENTION

The present invention generally relates to a stretch resistant plantar fascia support system. More particularly, the present invention relates to a stretch resistant plantar fascia support system that may be adhesively applied to a foot to provide relief from plantar fasciitis.

FIG. 1 is a dissected bottom view of a human foot 100 provided to illustrate some of the parts of a plantar fascia 110 located in the bottom of the human foot 100. As shown in FIG. 1, the plantar fascia 110 extends from about the location of the heel 101 to about the location of the ball 102 of the foot. The plantar fascia 110 includes medial plantar fascia 120, superficial tracts 130, a central component of the plantar fascia 140, and a lateral component of the plantar fascia 150. The separate portions of the plantar fascia 110 act as a shock absorber while walking and transfer tensile forces along the bottom of the foot 100.

FIG. 2 illustrates a simplified side view of tissue and bone structure in the human foot 100. As shown in FIG. 2, the human foot 100 includes the plantar fascia 110, a plantar calcaneus 160, a talus 162, a navicular 164, a cuneiform 166, a cuboid 168, metatarsals 170, phalanges 172, a sesamoid 174, a fat pad area 176, and an outer skin surface 178. From the side view in FIG. 2, the plantar calcaneus 160, the talus 162, the navicular 164, the cuneiform 166, the cuboid 168, the metatarsals 170, and the sesamoid 174 form what resembles the shape of an arch. This shape is commonly referred to as the longitudinal arch. Another arch commonly referred to as the transverse arch (metatarsal) also exists in about the same area in a perpendicular direction that runs laterally across the width of the foot.

The plantar fascia 110 serves the vital role of maintaining the shape of the two anatomical arches of the foot, the transverse arch and the longitudinal arch. As illustrated in FIGS. 1 and 2, the plantar fascia 110 runs across the bottom of the foot 100 from the heel 101 to the ball 102 and spreads out across the width of the foot 100. As longitudinal and lateral tensile stresses are produced in the bottom of the foot 100, the plantar fascia 110 absorbs the tensile forces and maintains the shape of the two anatomical arches.

For example, while standing or while in motion, forces experienced by the foot 100 act in a direction which tends to flatten the arches. The stress line 300 in FIG. 2 shows an approximation of the line of forces transferred through foot 100 during typical motion. As shown in FIG. 2, the stress line 300 resembles the shape of an archer's bow. The plantar fascia 110 running along near the bottom surface of the foot 100 is analogous to a string in the archer's bow. Forces that tend to move the ends of the bow apart increase tension on the string. In other words, as forces on the arch push the bones downward, the plantar fascia 110 is subjected to tensile forces.

If the tension on the plantar fascia 110 becomes excessive, the plantar fascia 110 may be damaged and produce a condition called plantar fasciitis. Plantar fasciitis is a painful medical condition resulting from inflammation of the plantar fascia 110. The plantar fascia 110 is thick and essentially inelastic. Overstressing the plantar fascia 110 may produce tears in the plantar fascia 110 or separate the plantar fascia 110 from bone and other surrounding materials. Tearing and separation of the plantar fascia 110 produces the painful inflammation known as plantar fasciitis. Frequently, the inflamed areas 305 are along the arch of the foot 100 or near the heel 101 of the foot 100 as shown in FIG. 2.

Plantar fasciitis may be quite debilitating in that everyday activities such as walking and standing may be very painful. Typical treatments for plantar fasciitis may involve oral anti-inflammatories, ice packs, bedrest, stretching, steroid injections, night splints and wedge-shaped arch supports. In extreme cases, treatment of plantar fasciitis may require corrective surgery.

For example, a design for an orthotic device for treatment of plantar fasciitis is disclosed in Gleason, U.S. Pat. No. 5,865,779. The device of Gleason is an elastic sock that is worn on a patient's foot. The elastic sock exerts compressive forces along the longitudinal and transverse axes of the patient's foot.

While some patients may be willing to wear an elastic sock, the elastic sock is both inconvenient and cumbersome. In order to be installed on the foot, the elastic sock must be stretched to fit over the heel and toe of the foot. Because the sock is elastic, the sock allows the foot to move and stretch. Consequently, the plantar fascia may still be subjected to excessive tensile forces during the critical healing process. Re-subjecting the plantar fascia to tensile forces before it has completely healed may re-aggravate damaged portions of the plantar fascia and undermine the healing process.

In addition, the elastic sock is meant to be worn multiple times and may require regular cleaning to avoid odors and foot infections. Also, the sock may not fit inside a shoe while being worn and may be considered unsightly while walking around with bare feet. Consequently, the elastic sock does not prevent excessive stretching of the plantar fascia and is both inconvenient and cumbersome.

Another typical example of treatment for plantar fasciitis includes medical personnel strapping strips of tape to the bottom of an injured foot. Strips of tape are applied at various angles across the bottom of the foot. The tape is difficult to remove from the rolls and bunches up during the taping process. Thus, care must be exercised during the application of the tape to avoid blister-causing wrinkles in the tape and other problems.

As the patient walks with the taped foot, the tape works loose and stretches with time. In addition, the tape cannot be effectively applied by the patient to the patient's own foot and requires application by another individual such as a trained medical technician. Consequently, taping the foot is cumbersome, inefficient, and ineffective in preventing excessive stretching of the plantar fascia.

Sometimes when current methods of treatment for plantar fasciitis are ineffective, expensive surgical procedures are required to relieve the pain of plantar fasciitis. To get at the plantar fascia, surgeons may perform either an endoscopic procedure requiring small incisions or conventional direct visualization requiring the underside of the foot to be opened up. With either painful procedure, scars may result and recovery time may be from weeks to months.

Even with treatment, improper treatment of plantar fasciitis may lead to other medical problems. For example, if inflammation near the heel is allowed to continue for a long period of time, calcium deposits may build-up in the damaged region. As the calcium builds-up, bony outcroppings may develop in the heel that are commonly referred to as "heel spurs". The longer the plantar fascia remains inflamed around the heel, the stronger the conditions are for the development of heel spurs. Protrusion of the heel spurs into the surrounding tissue may result in a cycle of irritation, inflammation, and pain known as heel spur syndrome.

Heel spur syndrome is commonly treated with a surgical procedure requiring removal of the heel spurs from within the foot. An endoscopic procedure is typically not used for removal of heel spurs and open surgery is typically required. Recovery time from such surgery may range from weeks to months, during which time the patient has to curtail the amount of stress placed on the foot.

Thus, it may be highly desirable to have a system for avoiding and/or treating the pain of plantar fasciitis. It may also be highly desirable to have a system for treating plantar fasciitis that is economical and may be easily applied by the patient. It may also be highly desirable to have a system for treating plantar fasciitis that is discretely attached to the sole of the patient's foot and includes a substantially stretch resistant material to reduce tensile forces in the plantar fascia.

BRIEF SUMMARY OF THE INVENTION

A preferred embodiment of the present invention provides a system for treatment of plantar fasciitis. The system is economical and may be easily applied by a patient.

A stretch resistant plantar fascia support system is provided with a foot sole support. The foot sole support may be a thin one-piece device made of a uniform substantially stretch resistant material of a uniform thickness or the foot sole support may be made with a strip of substantially stretch resistant material bounded by a more deformable material. The foot sole support may be shaped to conform to the outline of the bottom of a foot or shaped to cover only a portion of the bottom of a foot. Straps and tabs may be included with the foot sole support for providing additional support to both the foot and other portions of the stretch resistant plantar fascia support system. The foot sole support, straps, and tabs have adhesive applied to portions of the surface of the foot sole support, the straps, and the tabs. Removable protective covers are applied over the adhesive and the removable protective covers may include indicia signifying the order in which the portions of the stretch resistant plantar fascia support system are to be applied to the foot.

To relieve the symptoms of plantar fasciitis, tensile stresses in the plantar fascia are reduced. The tensile stresses in the plantar fascia are reduced by adhering the foot sole support to the foot of the patient. The foot sole support absorbs tensile stress in the lower foot thereby reducing the tensile stress experienced by the plantar fascia and surrounding tissues. The straps and tabs may be attached in the prescribed order to the foot sole support and wrapped around or attached to portions of the foot to provide additional support to the stretch resistant plantar fascia support system.

Certain embodiments of the present invention include an article of manufacture that is a kit for at least one of providing anatomical support to the arch of the foot, treating arch pain, treating heel pain, increasing tissue healing and rehabilitation in a human afflicted with plantar fasciitis, and preventing injury to the plantar fascia. The kit includes a sheet of material having a support layer, an adhesive layer for applying at least a portion of the support layer to the foot, and a cover layer that covers at least a portion of the adhesive layer and that may be removed from the support layer and adhesive layer. The kit includes instructions for applying the support layer to the foot for at least one of supporting the arch, reducing stress on the plantar fascia or surrounding tissues, and treating plantar fasciitis. The kit includes packaging carrying the sheet and instructions.

Certain embodiments of the present invention include a kit for managing foot pain. The kit includes a sheet of material configured to be affixed to at least a portion of a foot, the sheet including a stretch resistant support layer joined to a cover layer by adhesive, wherein the cover layer is removed from the adhesive and the support layer is affixed to the portion of the foot by the adhesive. The kit includes instructions instructing how to apply the support layer to the portion of the foot.

Certain embodiments of the present invention include a process for controlling stress on a plantar fascia of a foot. The process includes providing a sheet of material and instructions for using the sheet of material to control stress on the plantar fascia, wherein the sheet has a stretch resistant support layer joined to a cover layer by adhesive. The process includes reviewing the instructions, conforming the sheet of material to the shape of a portion of a foot, removing the cover layer from the adhesive and the support layer, applying the support layer to the portion of the foot such that the adhesive retains the support layer to the portion of the foot, and adjusting the support layer to the portion of the foot where the applying step results in an unsatisfactory application.

Certain embodiments of the present invention include an article of manufacture for managing foot pain. The article includes a sheet of material including a substantially stretch resistant Rayon support layer having a thickness of less than 15 mils, an adhesive layer, and a release liner. The sheet of material is configured to be conformed with cutting tools to the shape of at least a portion of the human foot. The support layer of the conformed sheet is affixed to the foot by the adhesive layer in order to control stress on the plantar fascia or support the arch of the foot.

Certain embodiments of the present invention include a sheet of material having a Rayon layer having a nominal thread count of 3600, a hypoallergenic adhesive on the layer, and a release liner affixed to the adhesive. The sheet of material has a thickness of less than 30 mils.

DETAILED DESCRIPTION OF PREFERRED EMBODIMENTS

Figure 1:
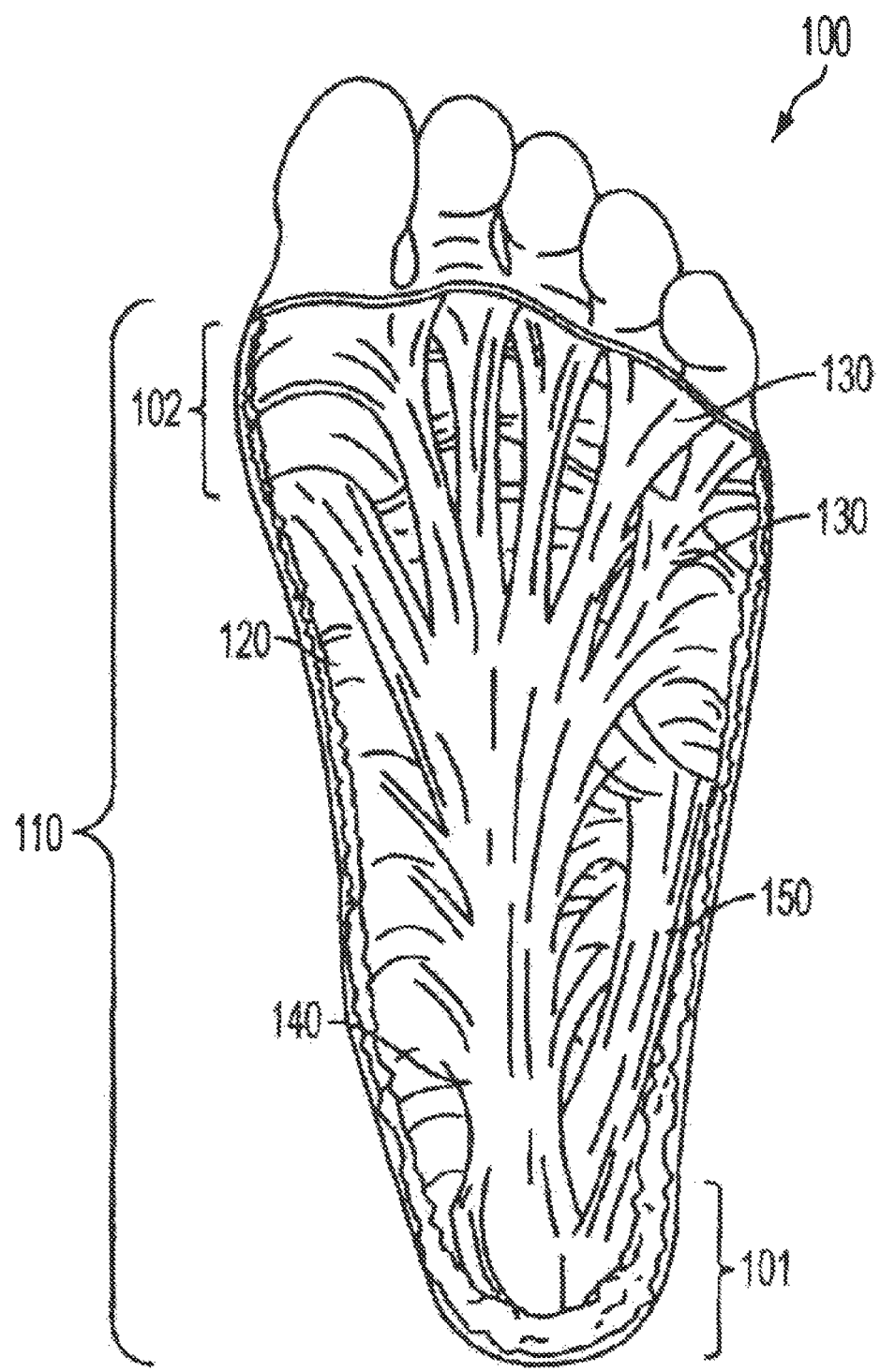
FIG. 1 illustrates parts of a plantar fascia in a dissected bottom view of a human foot.

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentality shown in the attached drawings.

Figure 3:
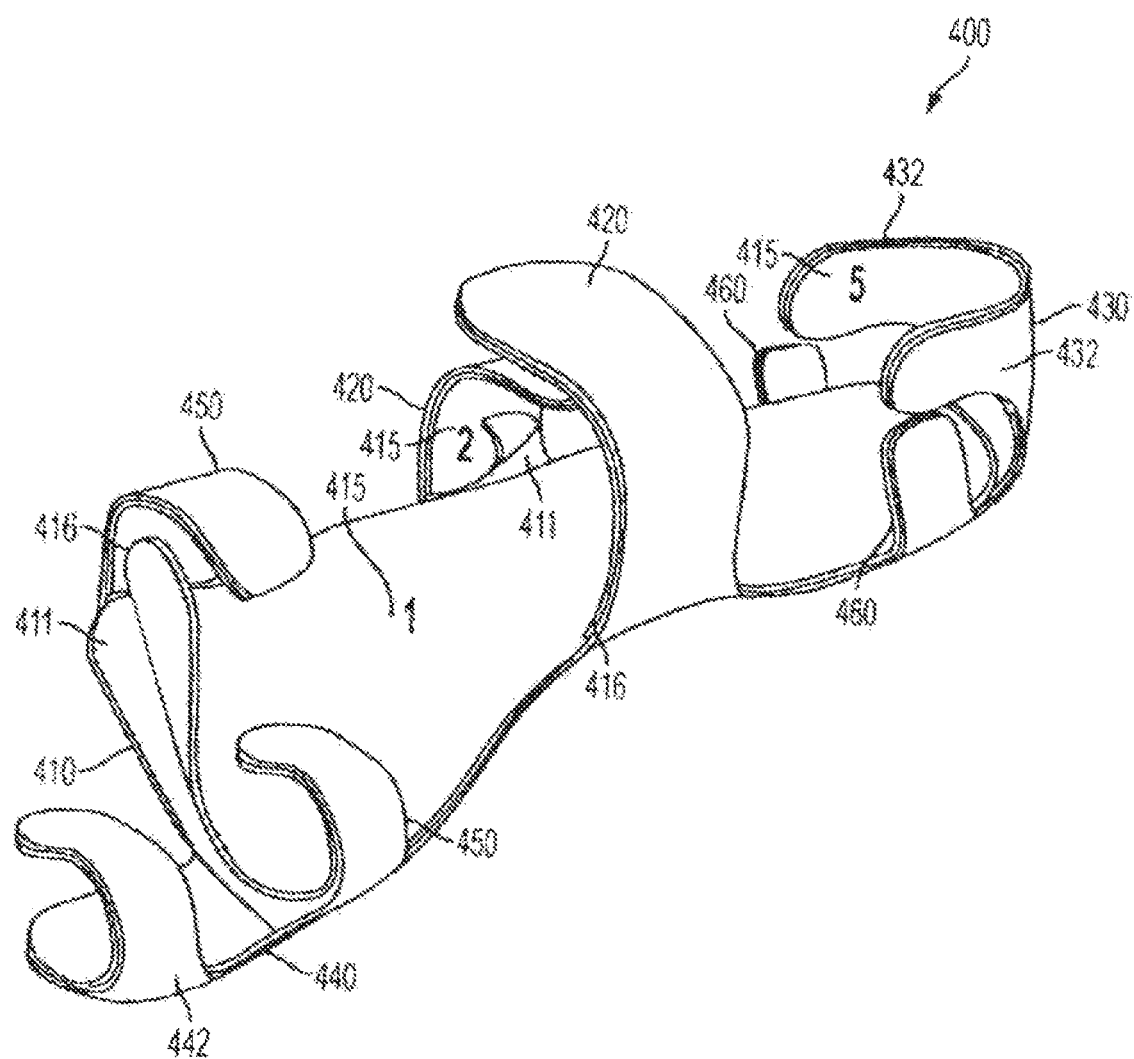
FIG. 3 illustrates a stretch resistant plantar fascia support system in accordance with an embodiment of the present invention.

FIG. 3 illustrates a stretch resistant plantar fascia support system 400 in accordance with an embodiment of the present invention. The stretch resistant plantar fascia support system 400 includes a foot sole support 410, an adhesive layer 411, indicia 415, removable protective covers 416, arch straps 420, heel strap 430, heel strap tabs 432, toe strap 440, toe strap tab 442, front straps 450, and heel tabs 460.

The arch straps 420, the heel strap 430, the toe strap 440, the front straps 450, and the heel tabs 460 are connected to the foot sole support 410. The arch straps 420 project from the sides of the foot sole support 410 approximately midway along the longitudinal axis of the foot sole support 410. The heel strap 430 projects from the back edge of the foot sole support 410 and the heel strap tabs 432 project from the sides of the heel strap 430. The toe strap 440 projects from the front edge of the foot sole support 410 and the toe strap tab projects from a side of the toe strap 440. The front straps 450 project from the sides of the of the foot sole support 410 adjacent the front edge of the foot sole support 410. The heel tabs 460 project from the sides of the foot sole support 410 adjacent the back edge of the foot sole support 410.

The adhesive layer 411 is applied to the top or inner surface of the foot sole support 410, the arch straps 420, the heel strap 430, the toe strap 440, the front straps 450, and the heel tabs 460. The removable protective covers 416 are removably adhered to the adhesive layer 411. Indicia 415 are printed on the removable protective covers 416.

In operation, the stretch resistant plantar fascia support system 400 is adhesively attached to a human foot 100. To adhesively attach the stretch resistant plantar fascia support system 400 to the human foot 100, the removable protective cover 416 adhered to the top of the foot sole support 410 is removed. The foot sole support 410 is pressed against the outer skin surface 178 on the bottom of the human foot 100.

Adhesion of the foot sole support 410 to the outer skin surface 178 on the bottom of the human foot 100 prevents extension and stretching of tissue on the bottom of the foot. By restricting extension of the tissue on the bottom of the foot, the level of tensile stress on the plantar fascia is reduced.

In the alternative, adhesive may be applied to select portions of the foot sole support 410, the straps 420, 430, 440 and 450, and the tabs 432, 442, and 462. For example, to reduce the chance of irritation to sensitive skin regions along an arch of the foot or to accommodate users with high arches, adhesive may only be applied to the portion of the foot sole support 410 contacting the ball of the foot and the heel of the foot.

In another alternative embodiment, adhesive may be applied to the sole of the foot. For example, adhesive sprays may be used to spray an adhesive layer on select portions of the foot. If a strong enough adhesive spray is used that would hold the foot sole portion 410 in place, then the stretch resistant plantar fascia support system 400 may be supplied without the adhesive layer 411 and removable protective covers 416.

To help maintain the position of the foot sole support 410 on the bottom of the human foot 100 and further reduce tensile stress on the plantar fascia, the arch straps 420 may be wrapped laterally over the arch of the foot. To install the arch straps 420, the removable protective cover 416 adhered to the inner surface of the arch straps 420 is removed. The arch straps 420 are then wrapped up and over the top of the foot 100. To secure the arch straps 420 in place, one of the arch straps 420 may overlap another arch strap 420 and be adhered to the outer surface of the other arch strap 420.

In the alternative, only one arch strap 420 may be used. With only one arch strap 420, the arch strap 420 may wrap laterally over the top of the arch and adhere to the bottom surface of the foot sole support 410 on the opposite side of the foot 100.

In another alternative embodiment, only one arch strap 420 may be used and the arch strap 420 may be separate and distinct from the foot sole support 410. With the foot sole support 410 already installed on the bottom of the foot 100, the arch strap 420 may be adhered to the foot sole support 410 on one side of the foot 100. The arch strap 420 may then be wrapped laterally over the arch, down the opposite side of the foot 100, and adhered to the foot sole support 410 on the opposite side of the foot 100.

Installation of the arch straps 420 also reduces stress on the plantar fascia. As presented earlier with regard to FIG. 2, the stress line 300 in FIG. 2 resembles an archer's bow. The stress line 300 passes through the talus 162, the navicular 164, the cuneiform 166, and the cuboid 168. Laterally wrapping the arch straps 420 over and around the top of the foot near the arch provides resistance to vertical and lateral movement of the talus 162, the navicular 164, the cuneiform 166, and the cuboid 168. Provision of the resistance to vertical and lateral movement by the arch straps 420 reduces flexure of the "bow" and related changes in stress on the plantar fascia.

To provide extra support to the heel of the human foot 100 and help maintain the position of the foot sole support 410 on the bottom of the human foot 100, the heel strap 430 may be adhered to the heel of the foot 100. To further support the heel and help maintain the position of the foot sole support 410, the heel strap 430 includes heel strap tabs 432. To install the heel strap 430 and heel strap tabs 432, the removable protective cover 416 adhered to the inner surface of the heel strap 430 and heel strap tabs 432 are removed. The heel strap 430 is then pressed against the back of the heel of the foot 100 and secured in place by contact between the adhesive layer 411 and the outer skin surface 178. The heel strap tabs 432 are pressed against the outer skin surface 178 along the sides of the heel of the foot 100.

In an alternative embodiment, the stretch resistant plantar fascia support system 400 may include a heel strap 430 without heel strap tabs 432. The heel strap 430 may be installed as described above by removing the removable protective cover 416 and adhering the heel strap 430 to the back of the heel.

Installation of the heel strap 430 provides extra support to the heel and helps maintain the position of the foot sole support 410. Adhesion of the heel strap 430 to the back of the heel provides an anchor point for the rear portion of the foot sole support 410. During the course of walking, the foot sole support 410 may be subjected to lateral and longitudinal forces from contact between the foot sole support 410 and other surfaces such as the interior of shoes or floor surfaces. Depending on the level of the lateral and longitudinal forces, the resistance to lateral and longitudinal forces provided by the adhesive layer 411 may be exceeded. Adhering the heel strap 430 to the heel of the foot 100 provides extra resistance to lateral and longitudinal forces that may otherwise cause the foot sole support 410 to shift around on the bottom of the foot.

Additionally, the heel strap 430 provides extra support to the heel of the foot 100. The human foot has a complex structure of tissue and bones. Tissues in the heel interact with other tissues in the foot to transfer forces exhibited during walking. As shown in FIG. 1, portions of the plantar fascia attach to the heel and other tissues that continue up around the back of the heel. Through these attachments, tissues in the heel transfer forces to and from the plantar fascia. Providing extra support to the heel of the foot 100 reduces the amount of stress transferred between the heel and the plantar fascia.

The stretch resistant plantar fascia support system 400 also includes heel tabs 460. Similar to the heel strap 430, the heel tabs 460 assist in maintaining the position of the foot sole support 410. To install the heel tabs 460, the removable protective covers 416 adhered to the inner surface of the heel tabs 460 are removed. The heel tabs 460 are then pressed against the sides of the heel of the foot 100 and secured in place by contact between the adhesive layer 411 and the outer skin surface 178. As the foot sole support 410 is subjected to lateral and longitudinal forces, the heel tabs 460 provide additional resistance to the lateral and longitudinal forces to help maintain the installed position of the foot sole support 410.

The stretch resistant plantar fascia support system 400 also includes front straps 450. The front straps 450 assist in maintaining the position of the foot sole support 410 and provide extra support to the area near the ball of the foot 100. To install the front straps 450, the removable protective covers 416 adhered to the inner surface of the front straps 450 are removed. The front straps 450 are then wrapped up and over the top of the foot 100. To secure the front straps 450 in place, one of the front straps 450 may overlap another front strap 450 and be adhered to the outer surface of the other front strap 450.

In the alternative, only one front strap 450 may be used. With only one front strap 450, the front strap 450 may wrap laterally over the top of the foot 100 and adhere to the bottom surface of the foot sole support 410 on the opposite side of the foot 100.

In another alternative embodiment, only one front strap 450 may be used and the front strap 450 may be separate and distinct from the foot sole support 410. With the foot sole support 410 already installed on the bottom of the foot 100, the front strap 450 may then be adhered to the foot sole support 410 on one side of the foot 100. The front strap 450 may then be wrapped laterally over the foot 100, down the opposite side of the foot 100, and adhered to the foot sole support 410 on the opposite side of the foot 100.

During the course of walking, the foot sole support 410 may be subjected to lateral and longitudinal forces from contact between the foot sole support 410 and other surfaces such as the interior of shoes or floor surfaces. Depending on the level of the lateral and longitudinal forces, the resistance to lateral and longitudinal forces provided by the adhesive layer 411 may be exceeded. Adhering the front straps 450 near the ball of the foot 100 provides extra resistance to lateral and longitudinal forces that may otherwise cause the foot sole support 410 to shift around on the bottom of the foot.

Installation of the front straps 450 also reduces stress on the plantar fascia. As shown in FIG. 1, portions of the plantar fascia attach to the ball of the foot and other portions such as the superficial tracts 130 continue past the ball of the foot 100 to the toe region. Due to the complex structure of tissue and bones in the human foot, tissues near the ball of the foot interact with other tissues in the foot to transfer forces induced during walking. Through the attachments near the ball of the foot, tissues near the ball of the foot transfer forces to and from the plantar fascia 110. Providing extra support near the ball of the foot 100 reduces the amount of stress transferred between the ball of the foot and the plantar fascia 110.

The stretch resistant plantar fascia support system 400 includes a toe strap 440. Installation of the toe strap 440 assists in maintaining the position of the foot sole support 410. To install the toe strap 440, the removable protective cover 416 adhered to the inner surface of the toe strap 440 is removed. The toe strap 440 is then pressed against the underside of the toe and the adhesive layer secures the toe strap 440 in place.

To further secure the toe strap 440 in place, the toe strap 440 includes a toe strap tab 442. To install the toe strap tab 442, the removable protective cover 416 adhered to the inner surface of the toe strap tab 442 is removed. The toe strap tab 442 is then wrapped up and over the top of the toe of the foot 100. The toe strap is wrapped back down the opposite side of the toe and adhered to the underside of toe strap 440 on the opposite side of the toe.

In the alternative, more than one toe strap tab 442 may be attached to the toe strap 440. For example, a second toe strap tab may be positioned opposite the toe strap tab shown in FIG. 3 on the opposite side of the toe strap 440. To install the toe strap tabs 442, the removable protective cover 416 adhered to the inner surface of the toe strap tabs 442 is removed. The toe strap tabs 442 are then wrapped up and over the top of the toe. To secure the toe strap tabs 442 in place, one of the toe strap tabs 442 may overlap the other toe strap tab 442 and be adhered to the outer surface of the other toe strap tab 442 similar to the arch straps 420 shown in FIG. 3.

In another alternative embodiment, only one toe strap tab 442 may be used and the toe strap tab 442 may be separate and distinct from the toe strap 440 and the foot sole support 410. With the toe strap 440 already installed on the bottom of the toe, the toe strap tab 442 may then be adhered to the toe strap 440 on one side of the toe. The toe strap tab 442 may then be wrapped laterally over the toe, down the opposite side of the toe, and adhered to the toe strap 440 on the opposite side of the toe.

The stretch resistant plantar fascia support system 410 may also include indicia 415 printed on the removable protective covers 416. The indicia 415 may represent instructions for the installation of the stretch resistant plantar fascia support system 410. For example, the indicia 415 may be numerical or alphabetic designations for the order in which portions of the stretch resistant plantar fascia support system 410 are to be installed. In FIG. 3, the indicia 415 on the removable protective cover 416 over the foot sole support 410 is the number "1" designating that the foot sole support 410 is to be installed first. The indicia 415 on the removable protective cover 416 on the arch straps 420 is the number "2" designating that the arch straps 420 are the next portion to be installed. Thus, the indicia may be increased or decreased incrementally to designate the order in which the portions of the stretch resistant plantar fascia support system 400 are to be installed.

In the alternative, letters or words may be used instead of numerals as the indicia 415 to designate the order in which the portions of the stretch resistant plantar fascia support system 400 are to be installed. For examples, letters "A", "B", and "C" or the words "First", "Second", and "Third" may be used to designate the order in which the first three portions are to be installed.

In the alternative, the indicia 415 may be printed on the various portions of the stretch resistant plantar fascia support system 400. For example, if an adhesive spray is applied to the skin rather than using an adhesive layer 411 and removable protective covers 416, the indicia 415 may be printed on the inner surface of components such as the foot sole support 410 and a consumer may still be able to see the indicia and determine the order of application.

In an alternative embodiment, the stretch resistant plantar fascia support system 400 may include the foot sole support 410 without the arch straps 420, the heel strap 430, the toe strap 440, and front strap 450 and the heel tabs 460. Similar to the embodiment shown in FIG. 3, the foot sole support 410 would be adhesively applied to the bottom surface of the foot.

In the alternative, the stretch resistant plantar fascia support system 400 may include various combinations of the arch straps 420, the heel strap 430, the toe strap 440, and front straps 450 and the heel tabs 460. For example, an alternative embodiment of the stretch resistant plantar fascia support system 400 may include the foot sole support 410 with arch straps 420. Another alternative embodiment of the stretch resistant plantar fascia support system 400 may include the foot sole support 410 with the heel strap 430. Yet another alternative embodiment of the stretch resistant plantar fascia support system 400 may include the foot sole support 410 with the toe strap 440. Consequently, various alternative embodiments of the stretch resistant plantar fascia support system 400 may be used that include the foot sole support 410 with different combinations of the arch straps 420, the heel strap 430, the toe strap 440, and front strap 450 and the heel tabs 460.

Figure 4:
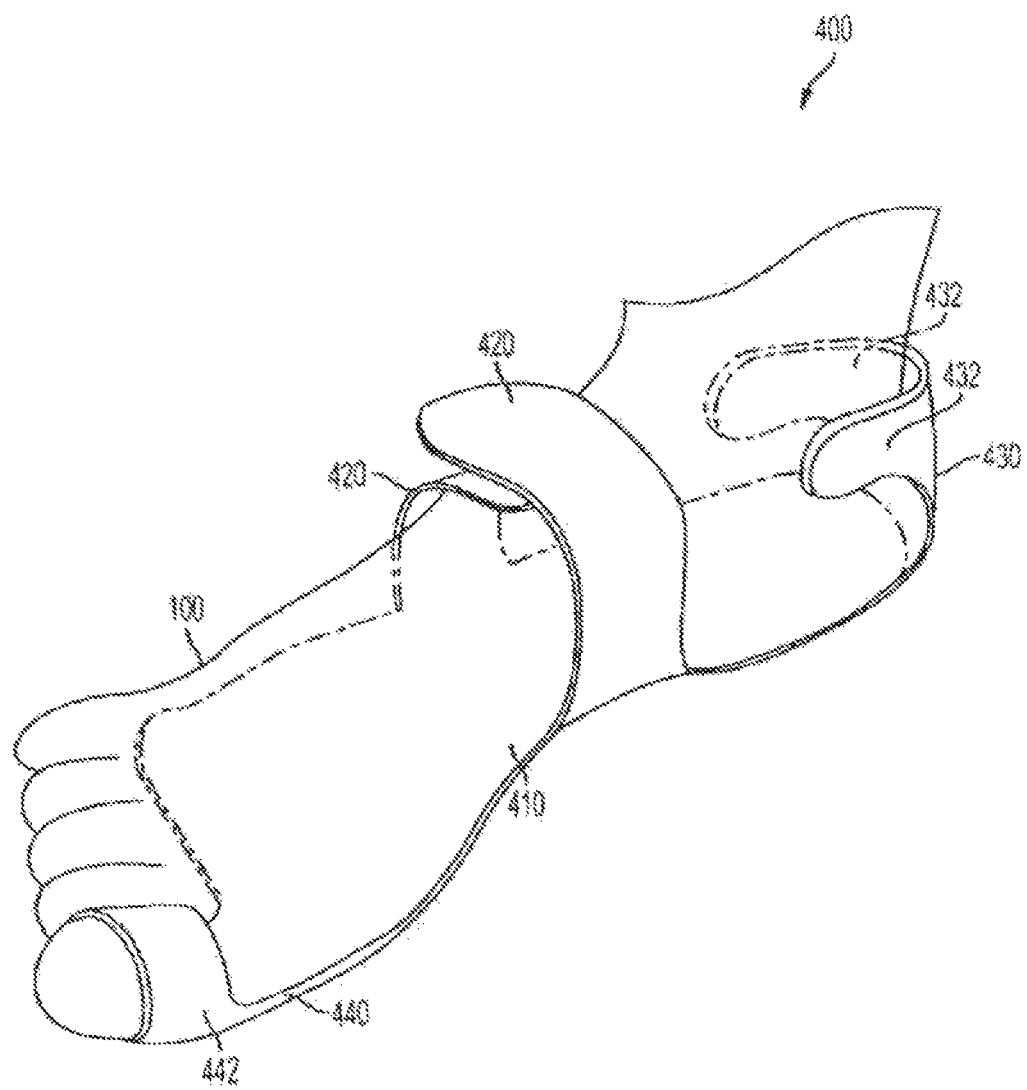
FIG. 4 illustrates a stretch resistant plantar fascia support system in accordance with an alternative embodiment of the present invention.

FIG. 4 illustrates a stretch resistant plantar fascia support system 500 as an alternative embodiment of the stretch resistant plantar fascia support system 400 of FIG. 3 installed on a human foot. The alternative embodiment shown in FIG. 4 includes a foot sole support 410, arch straps 420, heel strap 430, heel strap tabs 432, toe strap 440, and toe strap tab 442.

As shown in FIG. 4, the foot sole support 410 may be adhered to the sole of the foot to provide additional support to the region underneath the plantar fascia. The arch straps 420 may be wrapped around the top of the foot to provide additional support near the arch. The heel strap 430 may be adhered to the back of the heel to provide additional support to the heel and stabilize the position of the foot sole support 410. The toe strap 440 may be adhered to the bottom of the toe and the toe strap 442 wrapped around the toe to provide additional support to the toe and stabilize the position of the foot sole support 410.

Figure 2:
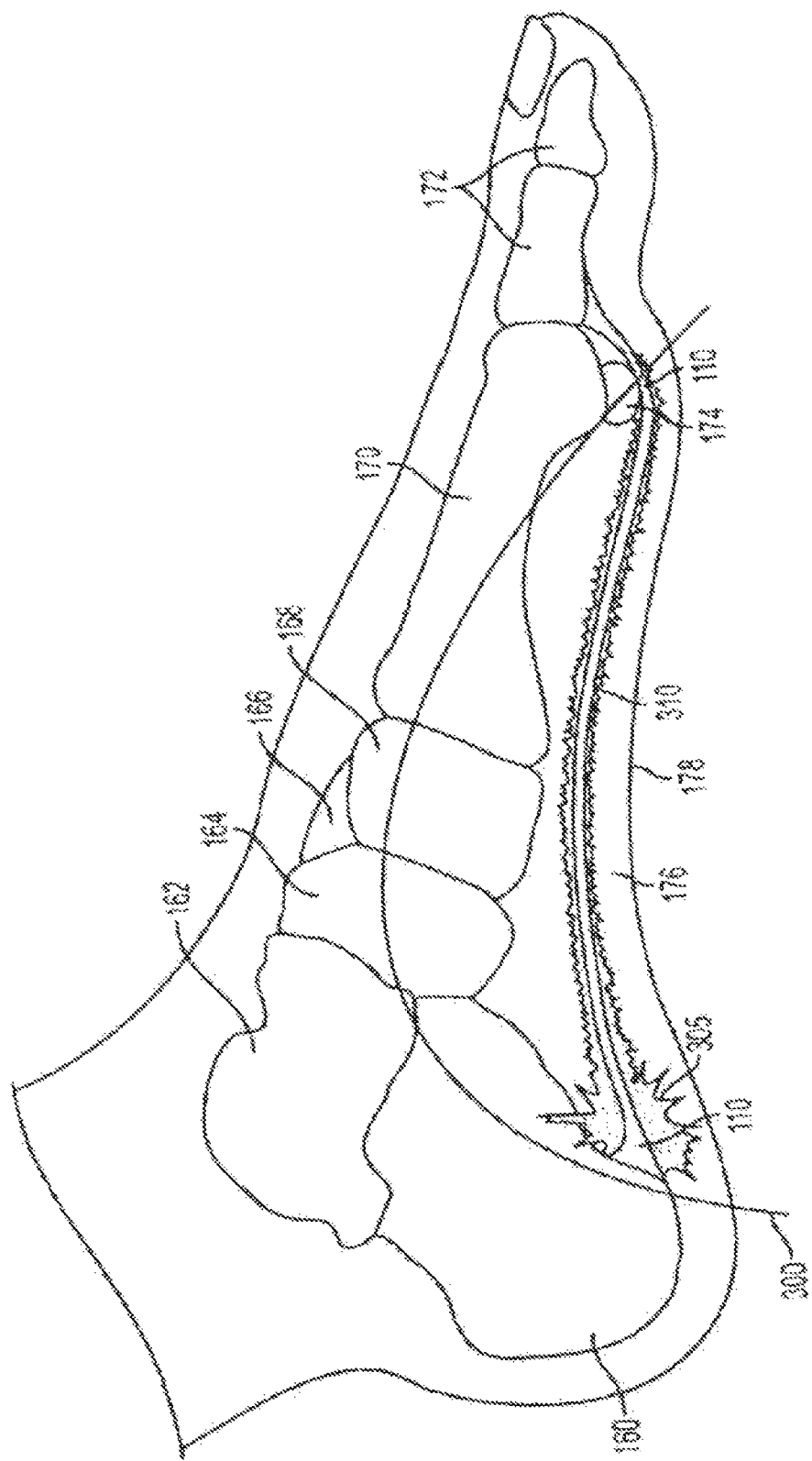
FIG. 2 illustrates a simplified side view of tissue and bone structure in the human foot.
Figure 5:
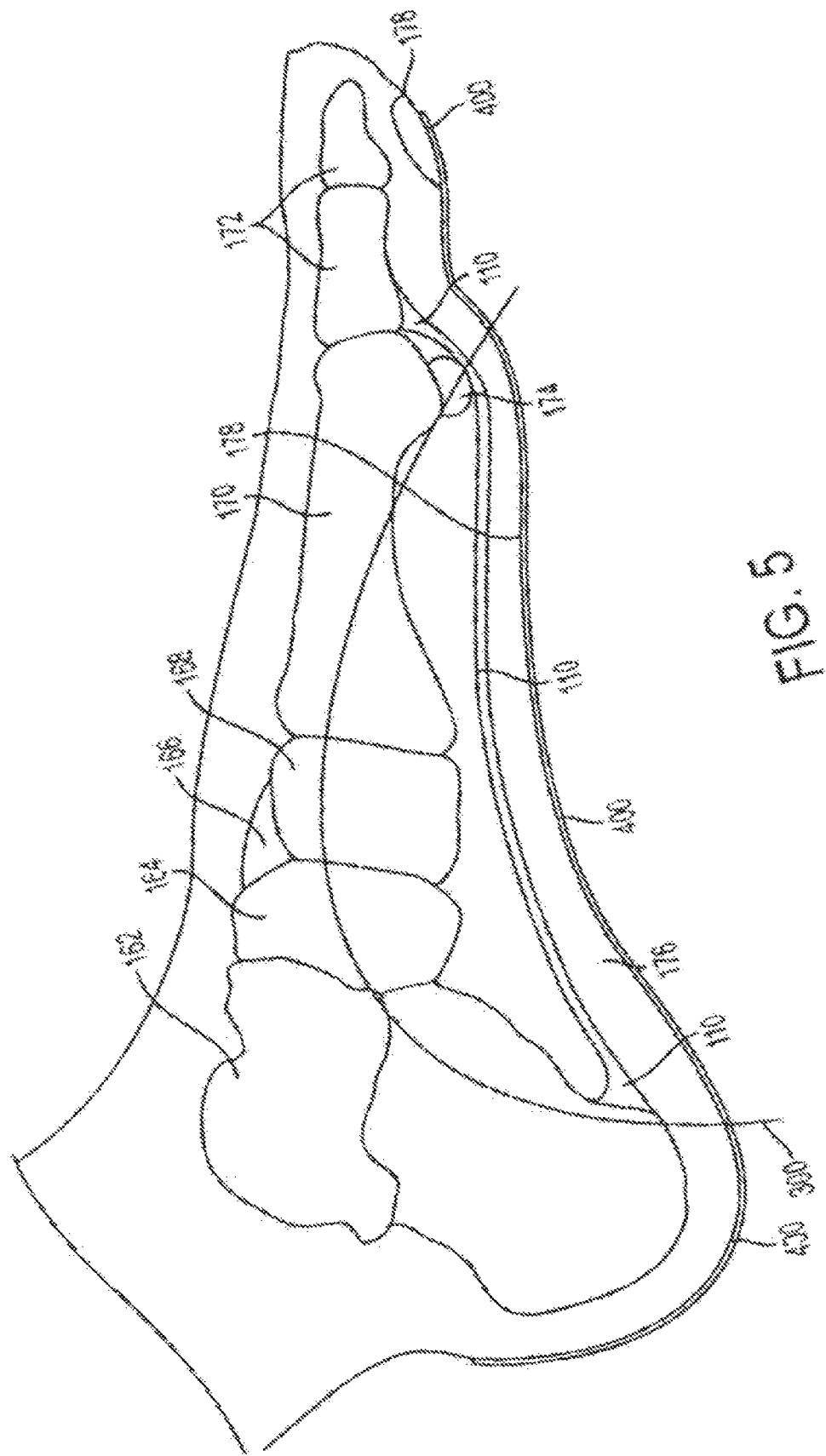
FIG. 5 illustrates stresses in the human foot with a stretch resistant plantar fascia support system installed in accordance with an embodiment of the present invention.

FIG. 5 illustrates stresses in the human foot 100 shown in FIG. 2 with a stretch resistant plantar fascia support system 400 attached to the human foot 100 in accordance with an embodiment of the present invention. As described previously with regard to FIG. 2, the stress line 300 shows an approximation of the line of forces transferred through a foot 100 during typical motion. The stress line 300 resembles the shape of an archer's bow. The plantar fascia 110 running along near the bottom surface of the foot 100 is analogous to a string in the archer's bow. Forces that tend to move the ends of the bow apart increase tension on the string. In other words, as forces on the arch push the bones downward, the plantar fascia 110 is subjected to tensile forces.

To reduce the tensile forces on the plantar fascia 110, the stretch resistant plantar fascia support system 400 is attached to the bottom of the foot. As depicted in FIG. 5, the stretch resistant plantar fascia support system 400 is analogous to another string in the archer's bow connected in parallel with the plantar fascia 110. Tensile forces induced in the bottom of the foot are shared between the plantar fascia 110 and the stretch resistant plantar fascia support system 400. Consequently, tensile force in the plantar fascia 110 is reduced and damaged areas may heal with a reduced likelihood of being subjected to excessive tensile forces.

Thus, a stretch resistant plantar fascia support system using a substantially stretch resistant material may be conveniently and easily applied to the foot of a patient by the patient for the treatment of plantar fasciitis. For example, the entire foot sole support, or portions of the foot sole support, of the stretch resistant plantar fascia support system may be made of a flexible material that exhibits less than 15 percent elongation when subjected to a 25 lb tensile load under test conditions specified in ASTM D3759. In addition, a material with a ratio of elongation to tensile strength (lb/in-width) that is less than 0.9 may be used to provide a balanced combination of strength and resistance to elongation.

Additionally, to simplify manufacturing and reduce cost, the stretch resistant plantar fascia support system may be made of a uniform material supplied in sheet form. Portions of the stretch resistant plantar fascia support system may be cut or punched from sheets of material. For example, the foot sole support may be shaped to resemble the outline of the sole of a left or right foot. Alternatively, the foot sole support may also be shaped for interchangeable use on either a left or right foot.

The stretch resistant plantar fascia support system may then be packaged individually, in multiples, or in a continuous package such as a roll with individual patches separated by perforations. For example, the individual packaging could be used by the average consumer for everyday use around the home. The continuous packaging could be used in high use situations such as locker rooms where access to stretch resistant plantar fascia support systems is required by multiple people.

Alternatively, the invention includes an article of manufacture that is an anatomical foot support kit for treating plantar fasciitis and other kinds of foot pain. The kit includes at least one sheet of stretch resistant material that can be adapted for application to the user's foot as a support system to treat plantar fasciitis, instructions that instruct the user on how to apply and use the support system, and packaging that allows for the distribution of the support system and instructions.

Figure 6:
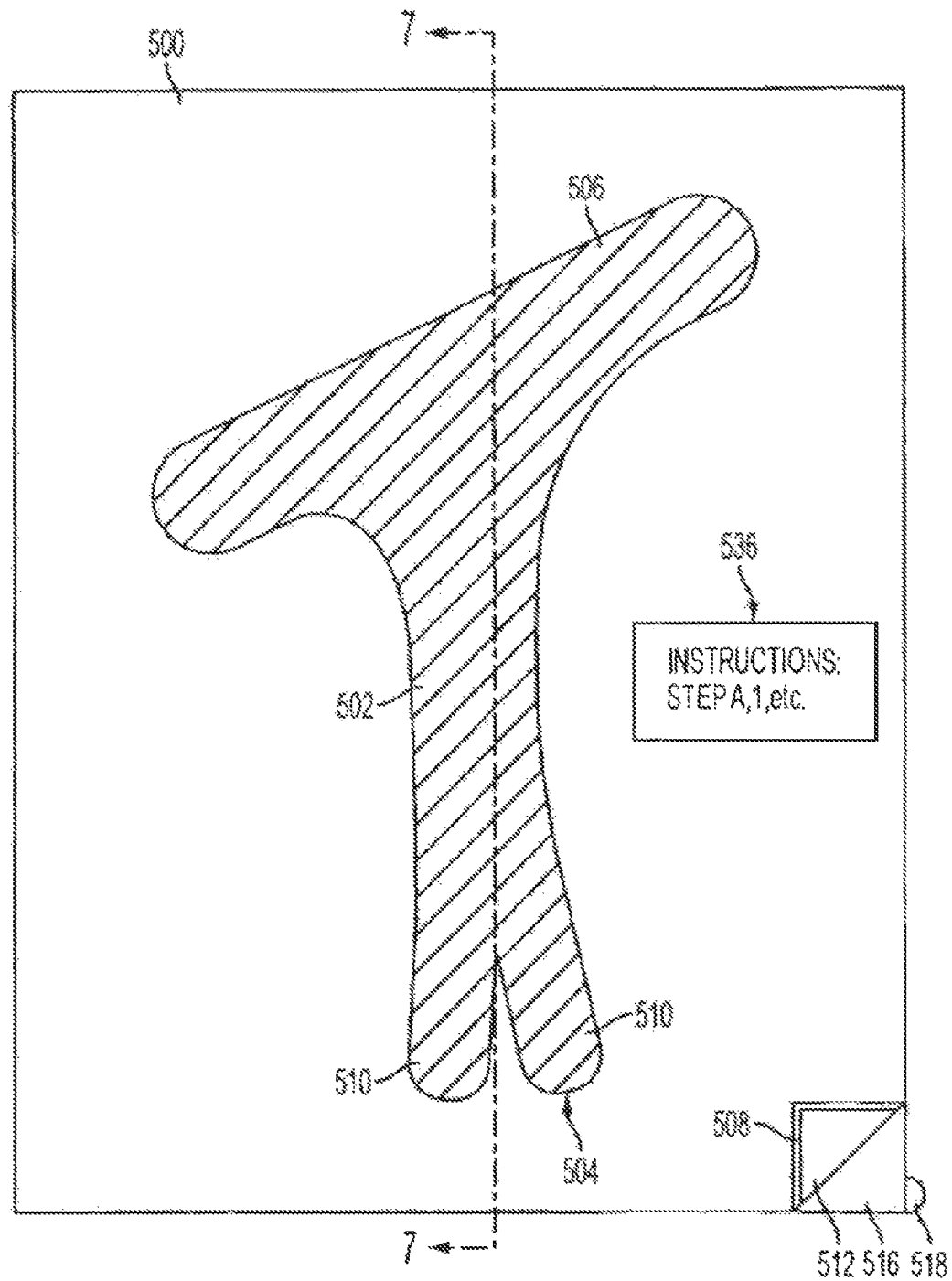
FIG. 6 illustrates a top view of a sheet of material containing a support system in accordance with an embodiment of the present invention.

FIG. 6 illustrates a top view of a sheet 500 of material. A support system 504 is formed and removed from the sheet 500 of material for use as the stretch resistant plantar fascia support system on the user's foot. The support system 504 is shaped to be applied to the user's foot or a portion of the foot. The support system 504 includes a sole portion 502 shaped for application to the sole of a foot, a ball strap 506 and heel tabs 510 for retaining the sole portion 502 to the foot or a portion of the foot. Alternatively, support system 504 may be shaped like the support system 400 shown in FIGS. 3 and 4 or have any number of other shapes for being connected to the user's foot. The support system 504 may be shaped for either a left or a right foot. The support system 504 may be pre-cut or perforated into the sheet 500 for the user to punch out of the sheet 500. Alternatively, the user may use cutting tools to cut the support system 504 from the sheet 500 along an outline imprinted on the sheet 500 or cut by freehand to suit the user's particular foot shape. The sheet 500 may be large enough to include more than one support system 504. Alternatively, the sheet 500 may be smaller such that the user may remove multiple smaller portions of a single support system 504 from the sheet 500 for application to the foot. The sheet 500 may be manufactured by a number of different techniques. Additionally, the sheet 500 may be pre-cut or perforated to form the support system 504 by a number of different techniques. By way of example only, the sheet 500 may be cut by die-cutting or laser cutting.

Figure 7:
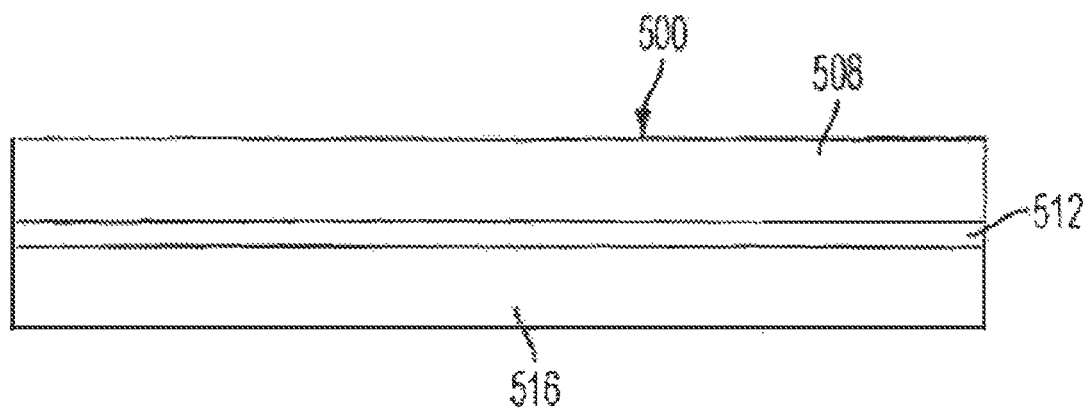
FIG. 7 illustrates an enlarged cross-sectional side view of the sheet of FIG. 6 taken along line 7-7.

FIG. 7 illustrates an enlarged cross-sectional side view of the sheet 500 of FIG. 6 taken along lines 7-7. Similar to the support system 400 of FIG. 3, the sheet 500 includes a backing or support layer 508, an adhesive layer 512, and a removable protective cover layer or release liner 516. Alternatively, the adhesive layer 512 may be an adhesive that is applied or coated to the support layer 508. The sheet 500 has a generally uniform thickness. By way of example only, the sheet 500 may have a thickness of up to ⅜ inch. By way of example only, the thickness of the sheet 500, including all three layers 508, 512, and 516, may be less than 60 mils. By way of example only, the thickness of the sheet 500, including all three layers 508, 512, and 516, may be less than 45 mils. The relative thicknesses of the layers 508, 512, and 516 may vary from each other differently from what is shown in FIG. 7.

Returning to FIG. 6, the support layer 508 is made of a material having the mechanical integrity to provide support under cyclic loading for the duration of application to the user's foot without excessive elongation, fraying or other forms of degradation. The support layer 508 is sufficiently flexible so that it can conform to the shape of the section of the foot to which it is adhesively connected and provide structural support to the body part. The material of the support layer 508 may be made of a single layer or a plurality of layers. By way of example only, the support layer 508 may be less than 15 mils thick and by further way of example may be less than 5 mils thick. The support layer 508 more easily conforms to the shape of the foot where the material of the support layer 508 is thinner. Additionally, the support layer 508 may also be compliant and non-irritating to the skin of the user. Furthermore, the support layer 508 may be of any color. For example, the support layer 508 may be tan or a skin-tone color such that the support layer 508 is less visible when applied to the user's foot.

The material of the support layer 508 is substantially stretch resistant in at least one direction. By way of example only, the support layer 508 may exhibit less than 15 percent total elongation in at least one direction when subjected to a 25 lb tensile load under test conditions specified in ASTM (American Society for Testing and Materials) D3759. In addition, by way of example only, the support layer 508 may have a ratio of elongation to tensile strength (lb/in-width) that is less than 0.9 to provide a balanced combination of strength and resistance to elongation. By way of example only, the support layer 508 may have a tensile strength of greater than 10 lb/in-width per ASTM D-1000 and by further way of example may have a tensile strength of greater than 20 lb/in-width per ASTM D-1000.

The support layer 508 may be manufactured from a wide range of materials such as woven and non-woven materials, polymeric materials such as apertured formed thermoplastic films, or apertured plastic films, synthetic or natural fibers, or a combination of materials. By way of example only, the support layer may be made of a woven rayon microfiber with a 3600 thread count and/or thickness of less than 30 mils, or alternatively less than 15 mils, such that the stretch resistant plantar fascia support system is thin enough to comply with the contours of the foot and strong enough to provide adequate strength.

Additionally, the support layer 508 may be breathable. By way of example only, the support layer 508 may have a moisture vapor transfer rate (MVTR) of at least 100 g/24 h/m·sup·2. By way of example only, the support layer 508 may have a MVTR of greater than 400 100 g/24 h/m·sup·2.

The adhesive layer 512 includes an adhesive that provides the requisite degree of adhesion to hold the support layer 508 against the user's foot for the duration of use and is relatively easy to remove at the end of use. The adhesive on the adhesive layer 512 is non-toxic and non-allergenic or hypoallergenic and may or may not be vapor permeable. The adhesive may provide enough tack such that the support layer 508 may be easily applied and re-adjusted to the foot if necessary. The adhesive is highly resistant to slippage or movement caused by the potentially high sheer stresses of the application. By way of example only, the adhesive layer 512 may be less than 10 mils thick, and by further way of example may be less than 5 mils thick. By way of example only, the adhesive may provide a holding strength of greater than 15 oz/in when tested according to a PSTC-3 (Pressure sensitive tape council) standard Adhesion-to-Steel 180 degree Peel test. By way of example only, the adhesive may provide a holding strength of greater than 30 oz/in when tested according to the Adhesion-to-Steel 180 degree Peel test.

The release paper 516 is provided over the adhesive layer 512. The release paper 516 should remain in place over the adhesive layer 512 until removed by the user. By way of example only, the release paper 516 may be made of 3.5 mil, 60 #Kraft paper. The release paper 516 may include a tab 518 that can be pulled to easily remove the release paper 516 from the adhesive layer 512. Alternatively, to case removal of the support layer 508 of the support system 504 from the release paper 516, the support layer 508 and the adhesive layer 512 that form the shape of the support system 504 may not be surrounded by any further support layers 508 or adhesive layers 512 on the release paper 516 such the surrounding release liner 512 is visible about the support system 504. Alternatively, the sheet 500 may be the shape of the support system 504 so that the support system 504 does not need to be removed from a larger sheet. Thus, the user can simply remove the release paper 516 from the sheet 500 in order to apply the support system 504.

Figure 8:
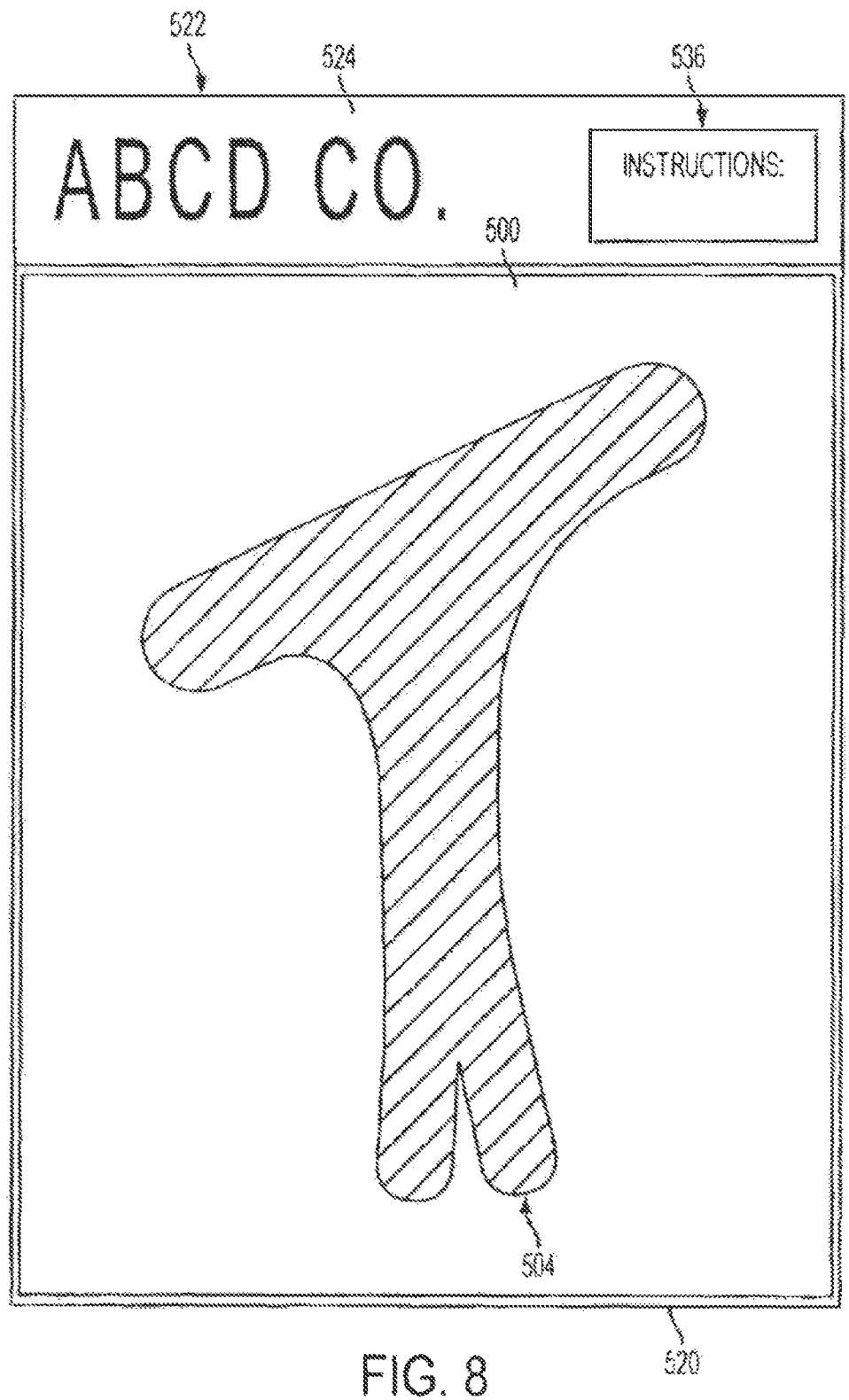
FIG. 8 illustrates a top view of a packaged anatomical foot support kit in accordance with an embodiment of the present invention.
Figure 9:
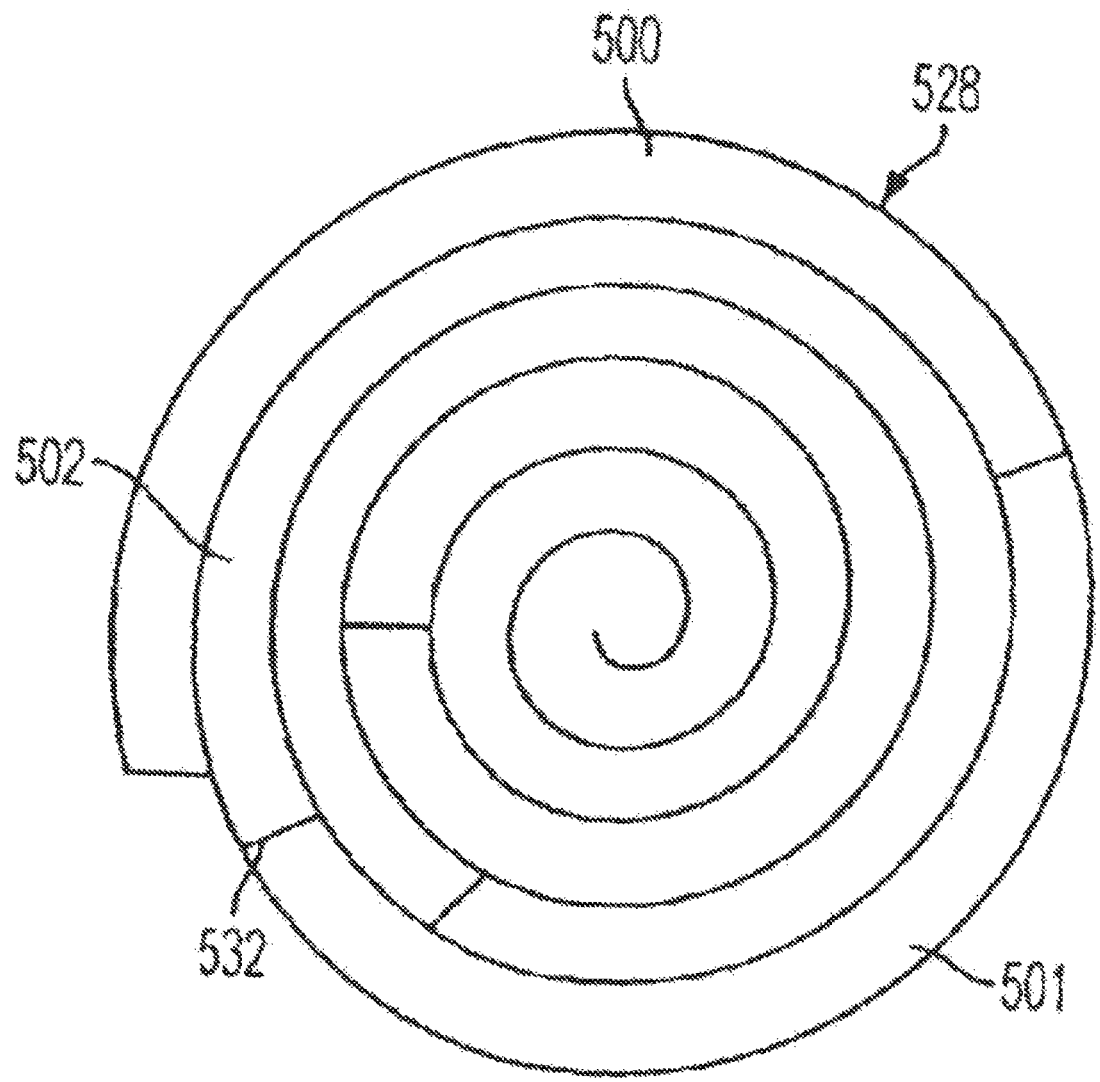
FIG. 9 illustrates a side view of an anatomical foot support kit in accordance with an embodiment of the present invention.

As shown in FIG. 8, the sheet 500 (or multiple sheets 500) may be provided in a package 522 for sales or distribution in stacked flat layers and sealed in a pouch or bag 520 with labeling 524. By way of example only, the bag 520 may be cellophane or another suitable material. Alternatively, as shown in FIG. 9, the sheet 500 (or multiple sheets 500) may be packaged by wrapping a plurality of sheets 500 about themselves in the shape of a roll 528. A specific sheet, bearing reference numeral 501, in a roll 528 is connected to an adjacent sheet, bearing reference numeral 502, in the roll 528 along a perforation 532. Alternatively, the user may unroll the sheets 500 and cut adjacent sheets 501 and 502 from each other. Alternatively, the roll 528 may include just one continuous sheet 500 wrapped about itself that the user may unwrap and cut where appropriate. The roll 528 may include a center spool (not shown) about which the sheet(s) 500 are wrapped. The roll 528 may be packaged in a labeled box or bag, or any number of other kinds of packaging.

Alternatively, the sheet 500 or multiple sheets 500 may be packaged in any number of other ways in boxes, bags, envelops, pouches, bottles, jars, cartons, packets, tubes, or any combination thereof or any number of other forms of packaging.

Figure 27:
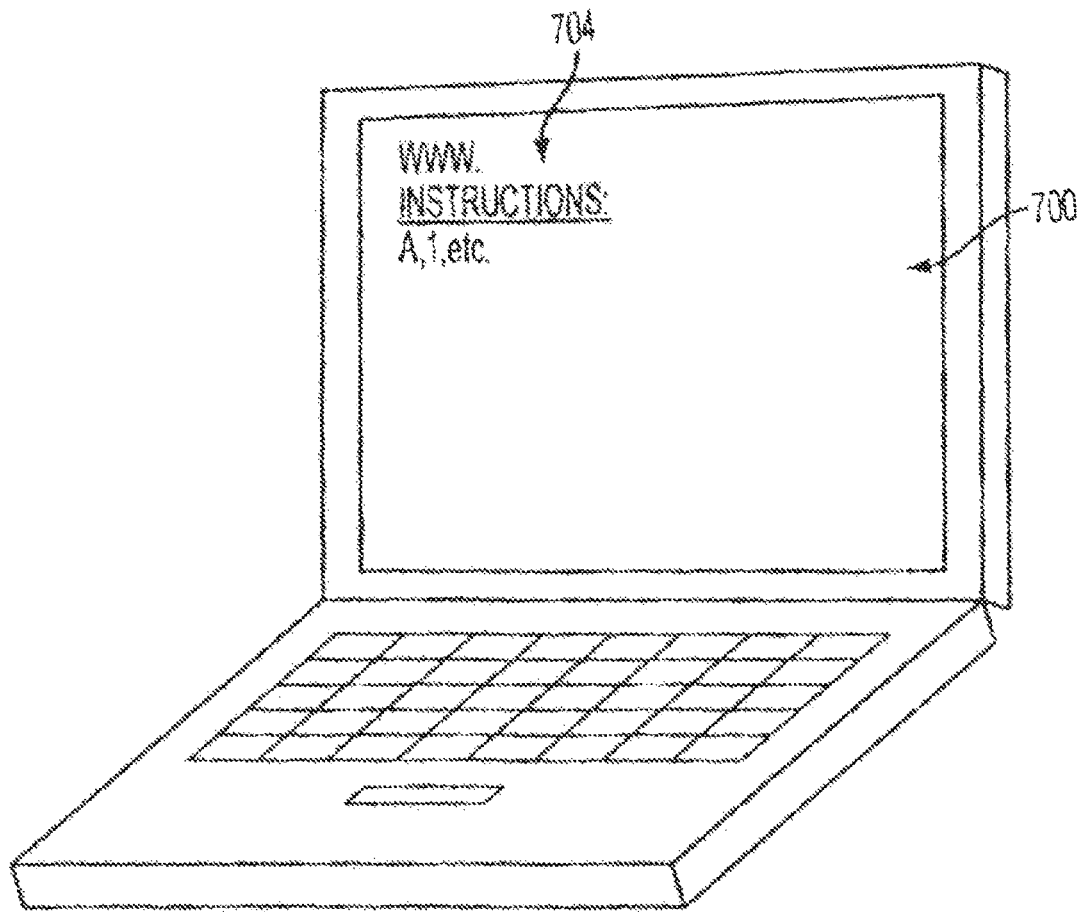
FIG. 27 illustrates a front view of a website showing instructions formed according to an embodiment of the present invention.

Returning to FIG. 6, instructions 536 are included with the sheet 500 instructing the user on how to apply and use the sheet 500 as a support system to treat plantar fasciitis. The instructions 536 instruct the user on how to cut or remove or shape the portion 504 to conform to the foot, and/or apply the portion 504 of material in a manner intended to provide anatomical support to the arch of the foot. As shown in FIG. 27, the instructions 536 may also direct the user to a specific computer internet website 700. The website 700 may provide a set of instructions 704 for cutting, removing, shaping and/or applying the portion 504 to the foot. The instructions 536 may also provide information on, or direct the user to a website 700 that provides information on, the causes and treatments of plantar fasciitis, and/or heel pain, and/or arch pain. Furthermore, the set of instructions 536 may contain, or direct the user to a website 700 that contains, other helpful and commonly known information regarding diagnosing or treating plantar fasciitis, heal pain and arch pain, including such items as stretching or therapeutic exercises, which may be used in combination with the support system of the sheet 500. The instructions 536 may be provided by a printed statement, indicia (such as alphabetical or numerical indicia similar to those shown in FIG. 3), a pattern, a photograph, an illustration, or an outline printed separately with, or directly on, the sheet 500 or portion 504. Alternatively, the instructions 536 may be provided on a brochure, print advertisement, card, manual, leaflet, or an electronic media storage device (such as a compact disc, digital video disc, memory stick, etc.) included in the packaging or the instructions 536 may be printed directly on the packaging 522 as shown in FIG. 8. Alternatively, the instructions 536 may be provided by any combination of the above.

Furthermore, the instructions 536 may direct the user to an interactive website 700 or other media where the user may further learn about the support system 504, plantar fasciitis, foot pain, arch pain, heal pain, and treatments and exercises. For example, the website 700 may provide the user with illustrations, descriptions of symptoms, and provide answers to questions to assist the user in confirming the diagnosis of plantar fasciitis. The website 700 may have numbered illustrations of the foot or sections of the foot that the user can select to describe the location of the pain. The website 700 may provide a questionnaire asking about the user's height, weight, age, flexibility, activities and activity level, changes in height or activity level, foot type (high arched, normal arched, flat footed), family history of plantar fasciitis, severity of pain, shoe sizes, shoes types and any number of other topics that will allow the website to advise the user on whether the user has plantar fasciitis and/or other kinds of foot pain or injuries such as a bruised heel, bunion, plantar wart, or any number of other problems. The website 700 helps the user determine whether the user actually has plantar fasciitis and thus whether the user should use the support system 504. People suffering from foot problems other than plantar fasciitis may not benefit from using the support system 504.

The interactive process of the website 700 provides the user with illustrations and instructions to help the user determine whether the user should use the support system 504 and determine the best size and shape of the support system 504 for the user to use. The interactive process may further instruct the user as to how to prepare the foot for application of the support system 504, such as by shaving or removing hair from the foot and removing oils and lotions from the foot. The interactive process may further instruct the user on the temperature at which to use the support system 504 and what tension levels are appropriate for use of the support system 504. The interactive process may further allow the user to chart and report progress in treating plantar fasciitis and answer questions the user may have during the course of the treatment. The interactive process may also provide methods to case removal of the support system 504.

The website 700 may also educate the user on the causes of stress on the plantar fascia and the factors which may contribute to plantar fasciitis such that the user may be able to change or alter activities that irritate or damage the plantar fascia. For example, the website 700 may inform users who climb stairs for exercise that such a practice may contribute to plantar fasciitis and provide ways to alter the user's behavior so as to reduce inflammation of the plantar fascia.

As part of the interactive process, the website 700 may provide the user with therapeutic exercises or stretches to perform while using the support system 504. Stretches which focus on the plantar fascia may be appropriate in later stages of treatment, and the interactive process may recommend exercises to the user at the appropriate point in the user's recovery that will further benefit the recovery. For example, because a biomechanical relationship exists between the calf muscle, the Achilles tendon, and the plantar fascia, the website may recommend exercises to stretch these areas while the user wears the support system such that the stress on the plantar fascia is controlled during stretching. The website 700 may recommend common calf-stretching exercises that incorporate the use of an angled board, stairs, a block, or a towel while wearing the support system 504. Examples of such exercises are described in American Family Physician, Vol. 63, Number 3, pages 469-470, the subject matter of which is incorporated herein by reference.

The interactive process of the website 700 may also suggest a particular shape or size of the support system 504 for the user based on the user's particular condition, footwear, or activities. By way of example only, the website 700 may recommend a support system 504 having a strapless sole portion 502 for a woman who wishes to wear open toed shoes. By way of example only, the website 700 may recommend a support system 504 having a sole portion 502, heel tabs 510, a ball strap 506 and an additional strap (not shown) for the arch of the foot to an overweight user who places a lot of weight to the arch of the foot. By way of example only, the website 700 may recommend a support system 504 having no straps across the arch of the foot to a runner that wears good arch-supporting running shoes.

In order to gain access to the interactive website 700, the user may be required to log-on with a code that is provided with the support system 504. Medical professionals such as doctors who are not the end users of the support system 504 may be allowed to enter and use the interactive website through separate method of access.

In operation, the user removes a sheet 500 from the packaging 522 of FIG. 8. The user may review the instructions 536 that come with the sheet 500 to learn how to apply and use the support system 504. The user removes or punches or cuts out the support system 504 from the sheet 500.

Figure 10:
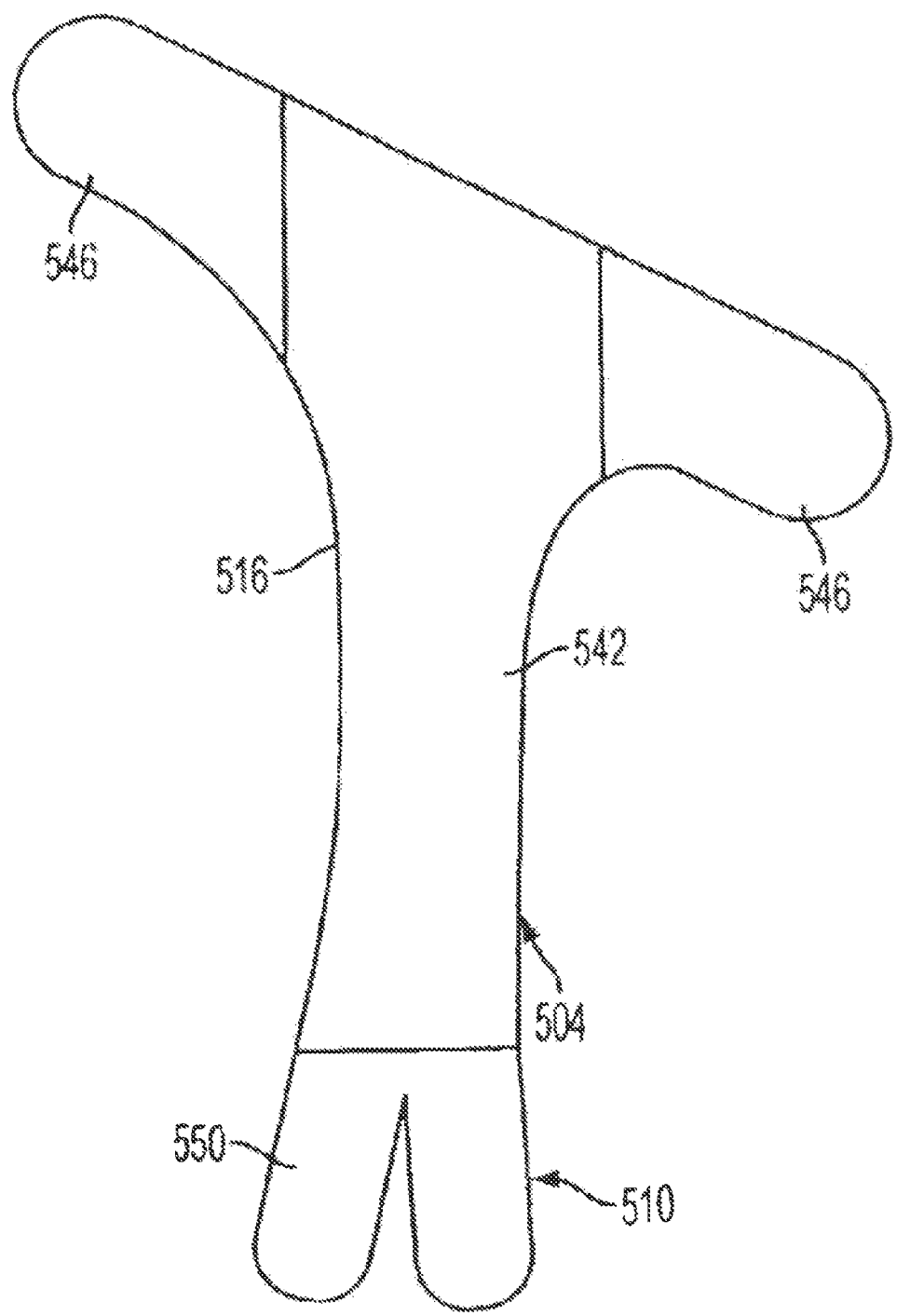
FIG. 10 illustrates a bottom view of a support system in accordance with an embodiment of the present invention.
Figure 11:
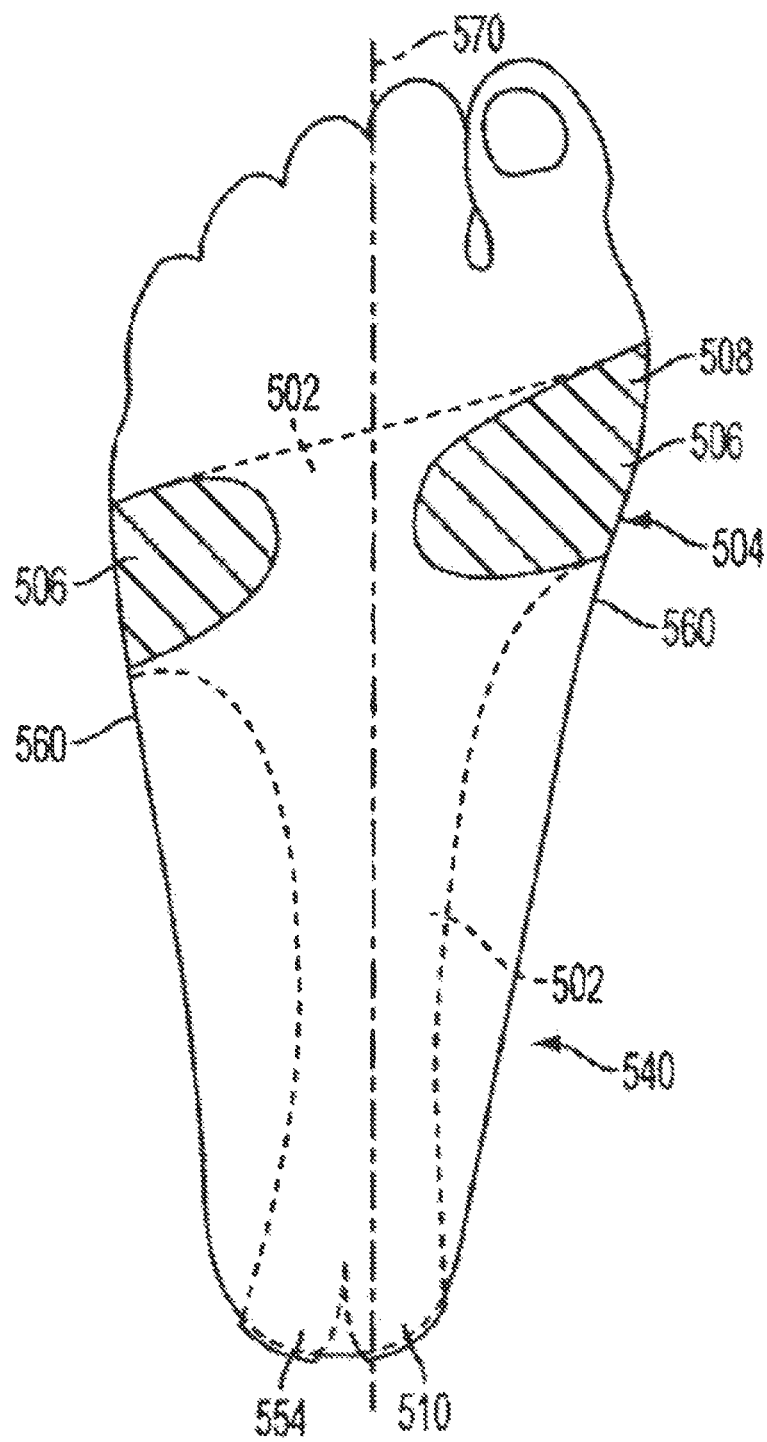
FIG. 11 illustrates a top view of a foot having the support system of FIG. 10 affixed to the foot.
Figure 12:
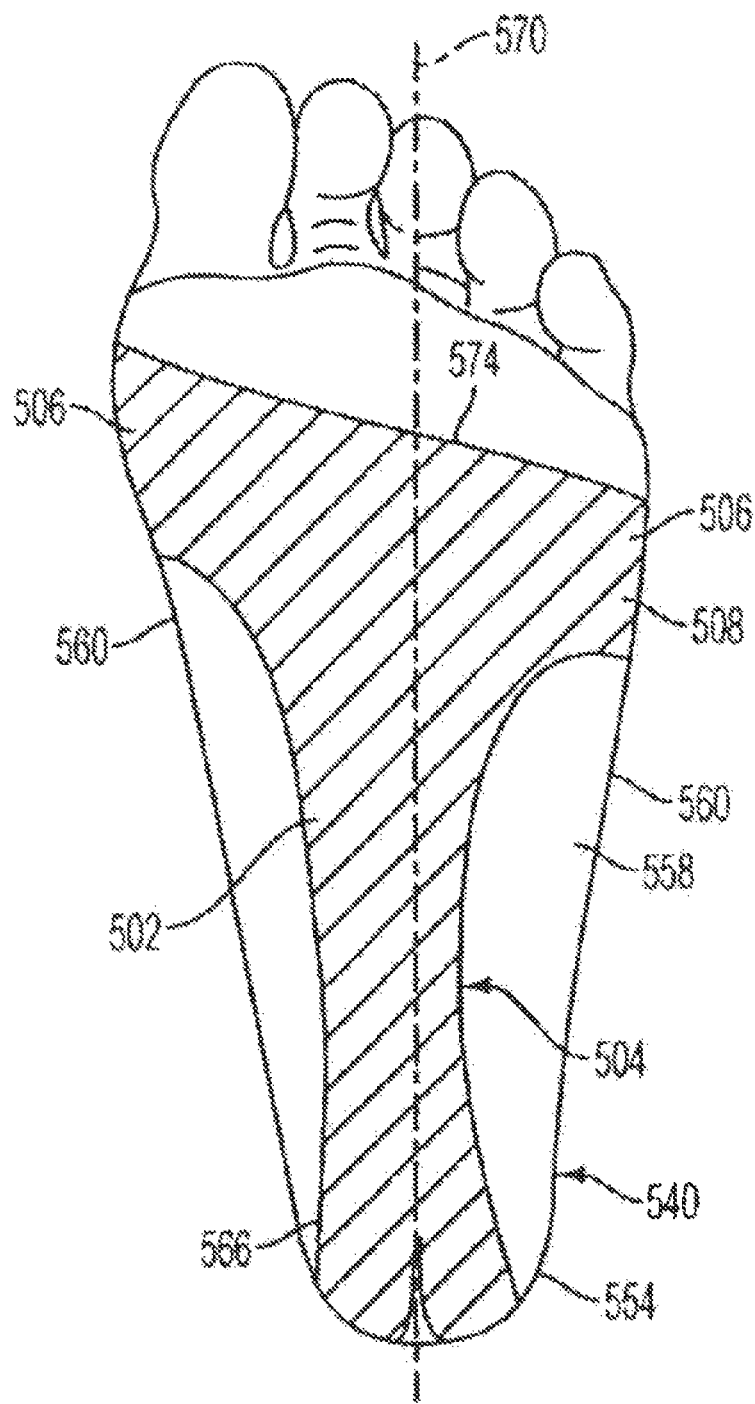
FIG. 12 illustrates a bottom view of the foot and support system of FIG. 11.
Figure 13:
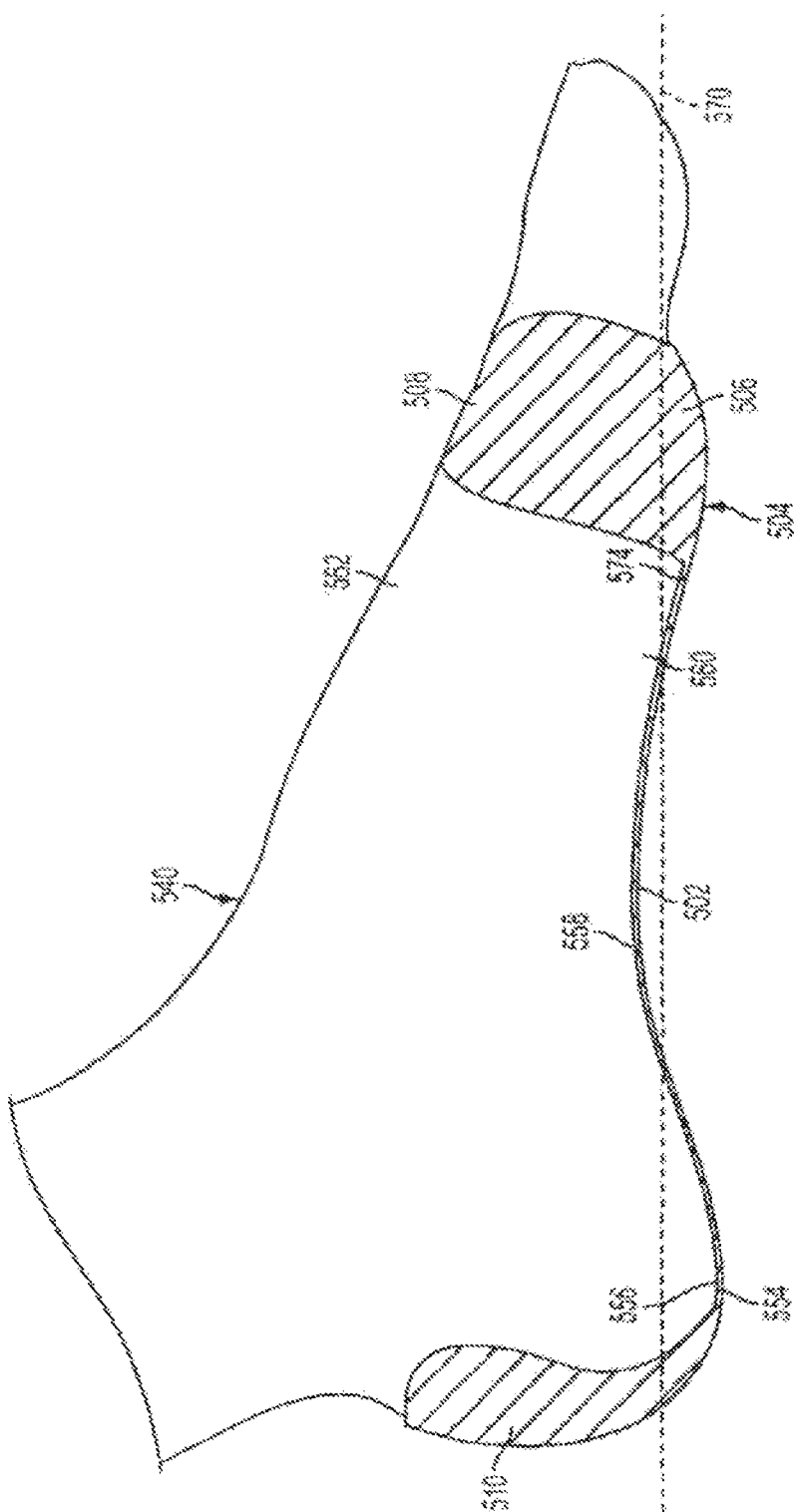
FIG. 13 illustrates a side view of the foot and support system of FIG. 11.
Figure 14:
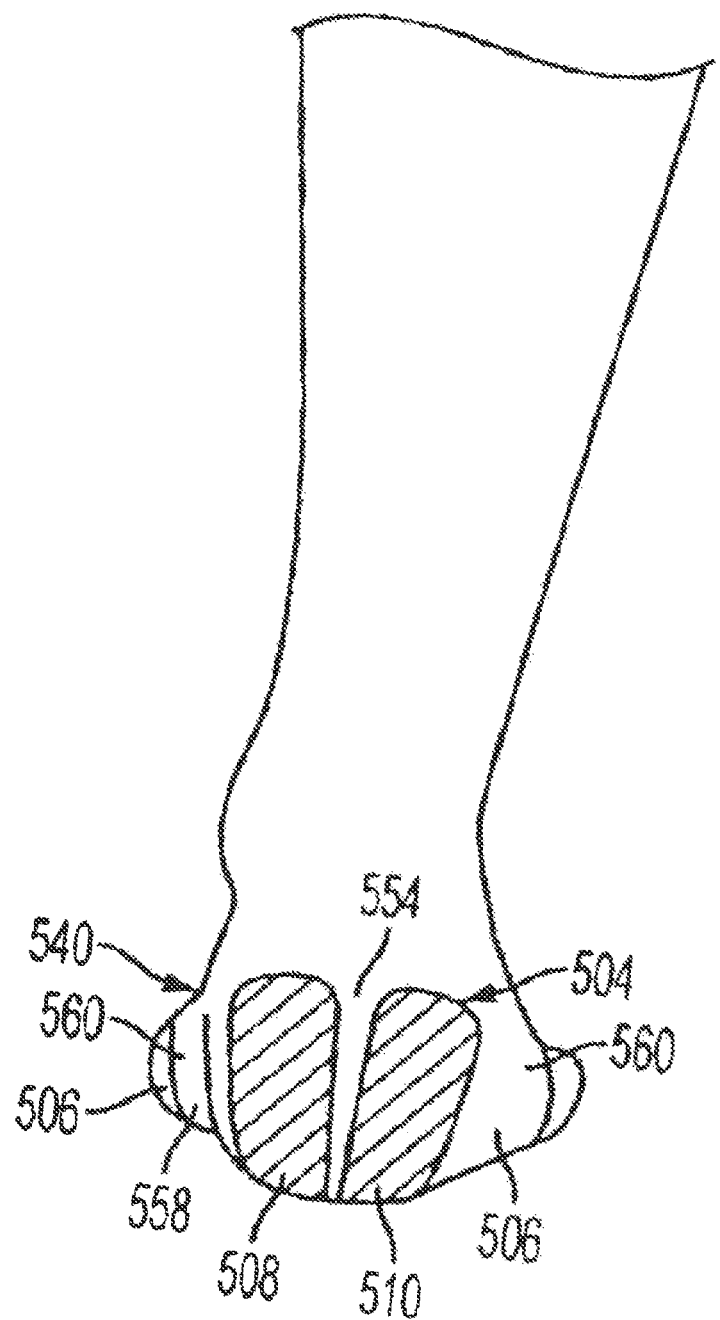
FIG. 14 illustrates a rear view of the foot and support system of FIG. 11.

Referring to FIG. 10, a support system 504 has been removed from the sheet 500. A release liner 516 is separated or perforated into a sole section 542, strap sections 546, and a tab section 550 such that different sections of the release liner 516 may be removed from the support system 504 as necessary. Alternatively, the release liner 516 may have any number of sections as necessary to accommodate the shape and use of the support system 504. After removing the support system 504 from the sheet 500, the user may further cut and form the support system 504 as necessary for application. For example, the user may trim the heel tab 510 such that the heel tab 510 better fits the user's foot.

Referring to FIGS. 11-14, a support system 504 is applied to a foot 540 or a portion of the foot 540. The user peels the tab section 550 (FIG. 10) of the release liner 516 (FIG. 7) from the heel tab 510 of the support system 504 and applies the heel tab 510 of the support layer 508 to the heel 554 of the user's foot 540 such that the adhesive layer 512 (FIG. 7) is affixed to the skin of the user's heel 554 and retains the support layer 508 to the heel 554. The user then peels the sole section 542 of the release liner 516 from the sole portion 502 of the support system 504 and adhesively applies the sole section 542 of the support layer 508 to the sole 558 of the user's foot 540. The sole portion 502 should be positioned about the sole 558 of the foot 540 from the bottom 566 of the heel 554 along a longitudinal axis 570 axis of the foot 540 to the ball 574 of the foot 540. The user then peels the strap sections 546 of the release liner 516 from the ball strap 506 of the support system 504 and adhesively applies the ball strap 506 of the support layer 508 transversely to the longitudinal axis 570 of the foot 540 across the sole 558 of the foot 540 about the sides 560 and top 562 of the user's foot 540 to secure the sole portion 502 about the sole 558. Thus, the multiple sections of the release liner 516 allow the user to use the heel tab 510 as an anchoring connection to the foot 540 such that the sole section 542 and the ball strap 506 may be more easily aligned and affixed to the foot 540 than if the entire support layer 508 was applied to the foot 540 at once. The user may remove and re-apply or adjust the support layer 508 on the foot 540 to obtain a better placement. Once the support layer 508 has been secured to the foot 540 as shown in FIGS. 11-14, the support layer 508 may be worn all day long and changed on a daily basis. The support system 504 may be used continuously or on a periodic basis as needed. Once each support layer 508 has been used, the user removes and disposes of the support layer 508 and reapplies a new support layer 508. The support layer 508 may be used with orthotic practices, physical therapy, and other treatment modalities to treat plantar fasciitis and other foot pain.

Figure 15:
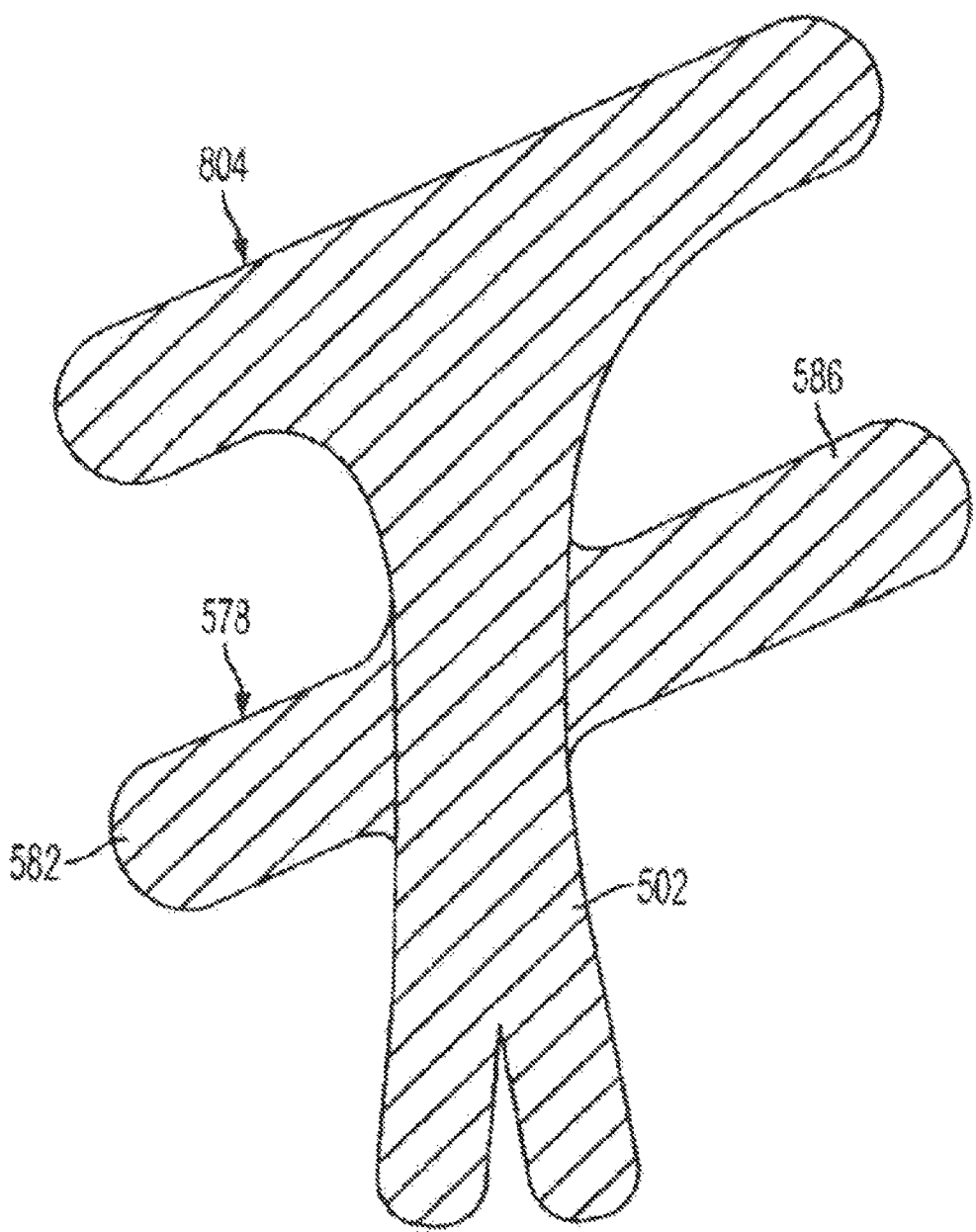
FIG. 15 illustrates a bottom view of a support system in accordance with an embodiment of the present invention.
Figure 16:
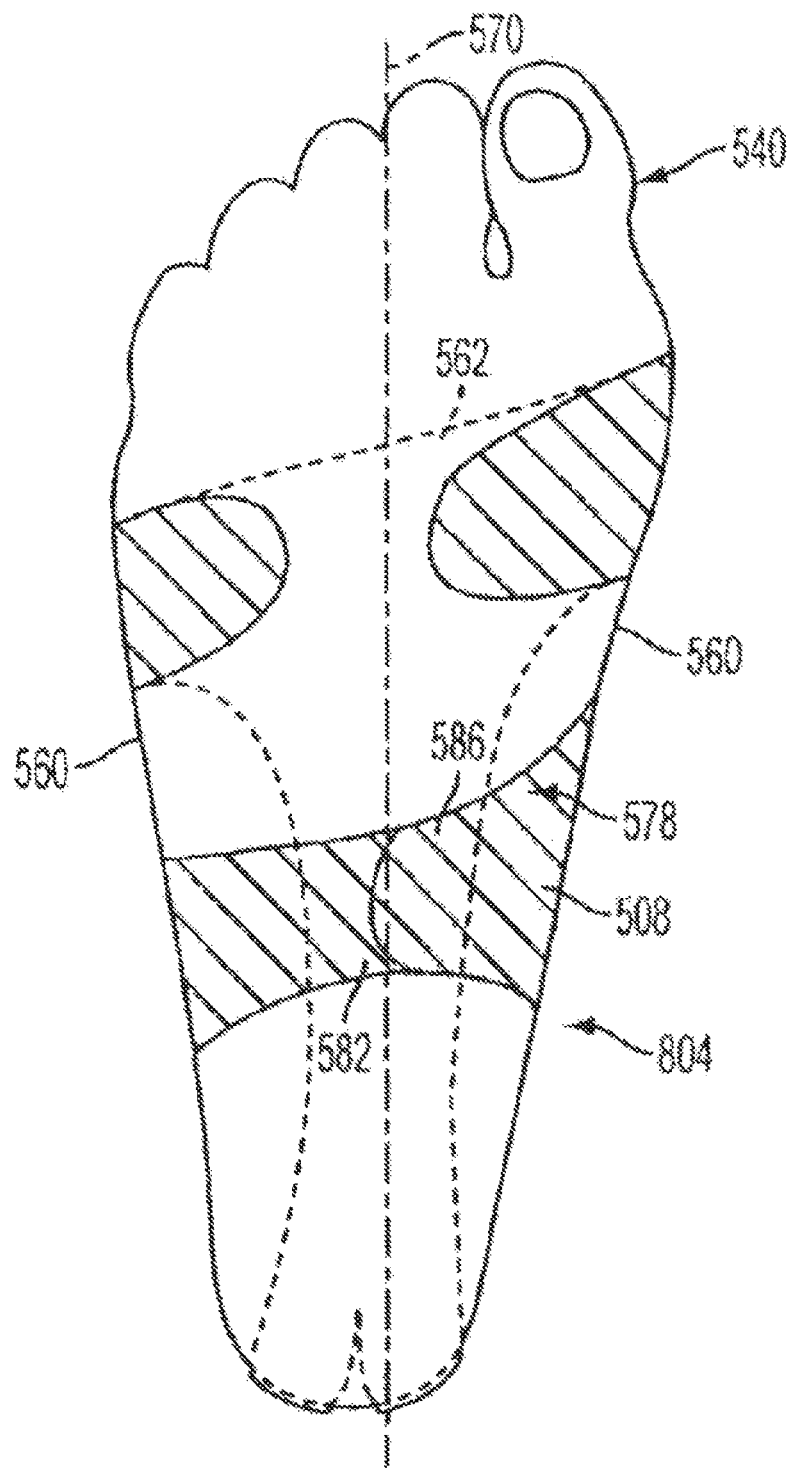
FIG. 16 illustrates a top view of a foot and the support system of FIG. 15 affixed to the foot.
Figure 17:
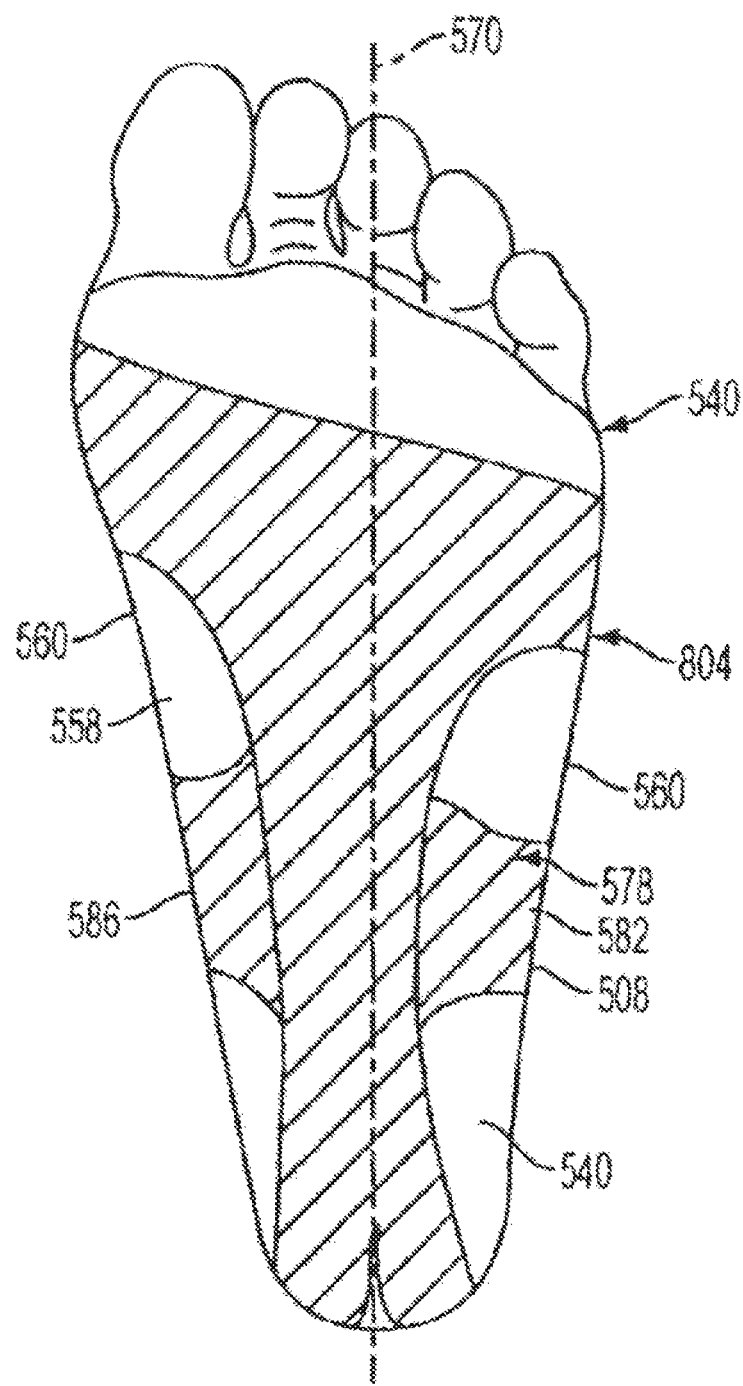
FIG. 17 illustrates a bottom view of the foot and support system of FIG. 15.
Figure 18:
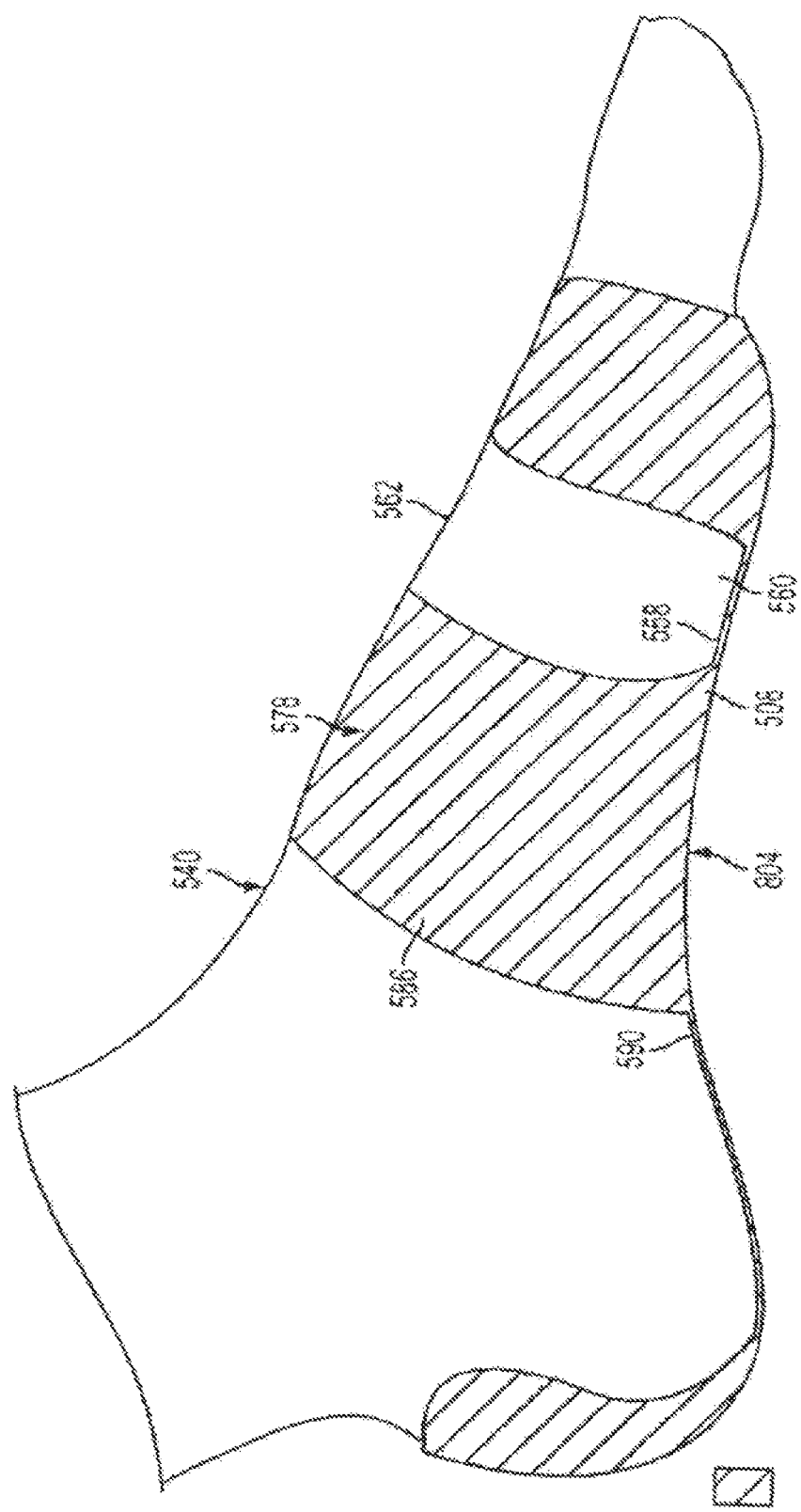
FIG. 18 illustrates a side view of the foot and support system of FIG. 15.

Alternatively, the support system may have any number of different configurations for use with a foot. Referring to FIG. 15, a support system 804 includes an additional arch strap 578 having first and second ends 582 and 586 extending transversely from the sole portion 502. FIGS. 16-18 illustrate multiple views of the support system 804 of FIG. 15 applied to a foot 540. The support system 804 is applied to the foot 540 in generally the same manner as the support system of FIGS. 11-14. However, the user also adhesively applies the arch strap 578 of the support layer 508 transversely to the longitudinal axis 570 and arch 590 of the foot 540 across the sole 558 of the foot 540 and about the sides 560 and top 562 of the user's foot 540 such that the first and second ends 582 and 586 may or may not overlap and are adhesively connected at the top 562 of the user's foot 540. The embodiment of the support system 804 with the arch strap 578 provides additional support along the arch 590 of the foot 540.

Figure 19:
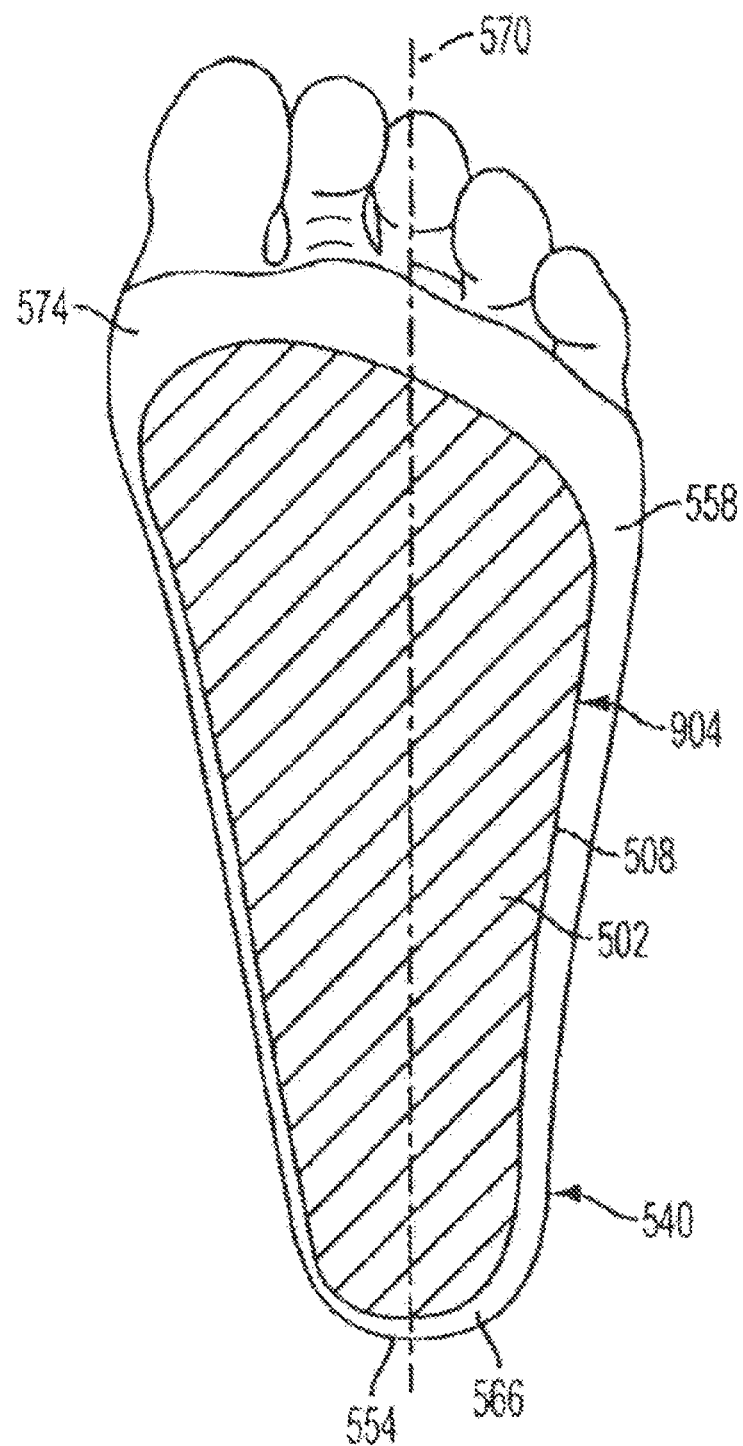
FIG. 19 illustrates a bottom view of a foot and a support system in accordance with an embodiment of the present invention.

Referring to FIG. 19, a support system 904 may include a strapless sole portion 502 that is adhesively applied to the entire sole 558 of the foot 540 from the bottom 566 of the heel 554 along the longitudinal axis 570 axis of the foot 540 to the ball 574 of the foot 540. Alternatively, the sole portion 502 may only cover a portion of the sole 558. Because the support system 904 does not include any straps, users may discretely wear the support system 904 with shoes that reveal the top and sides of the user's foot, such as sandals or other open shoes.

Figure 20:
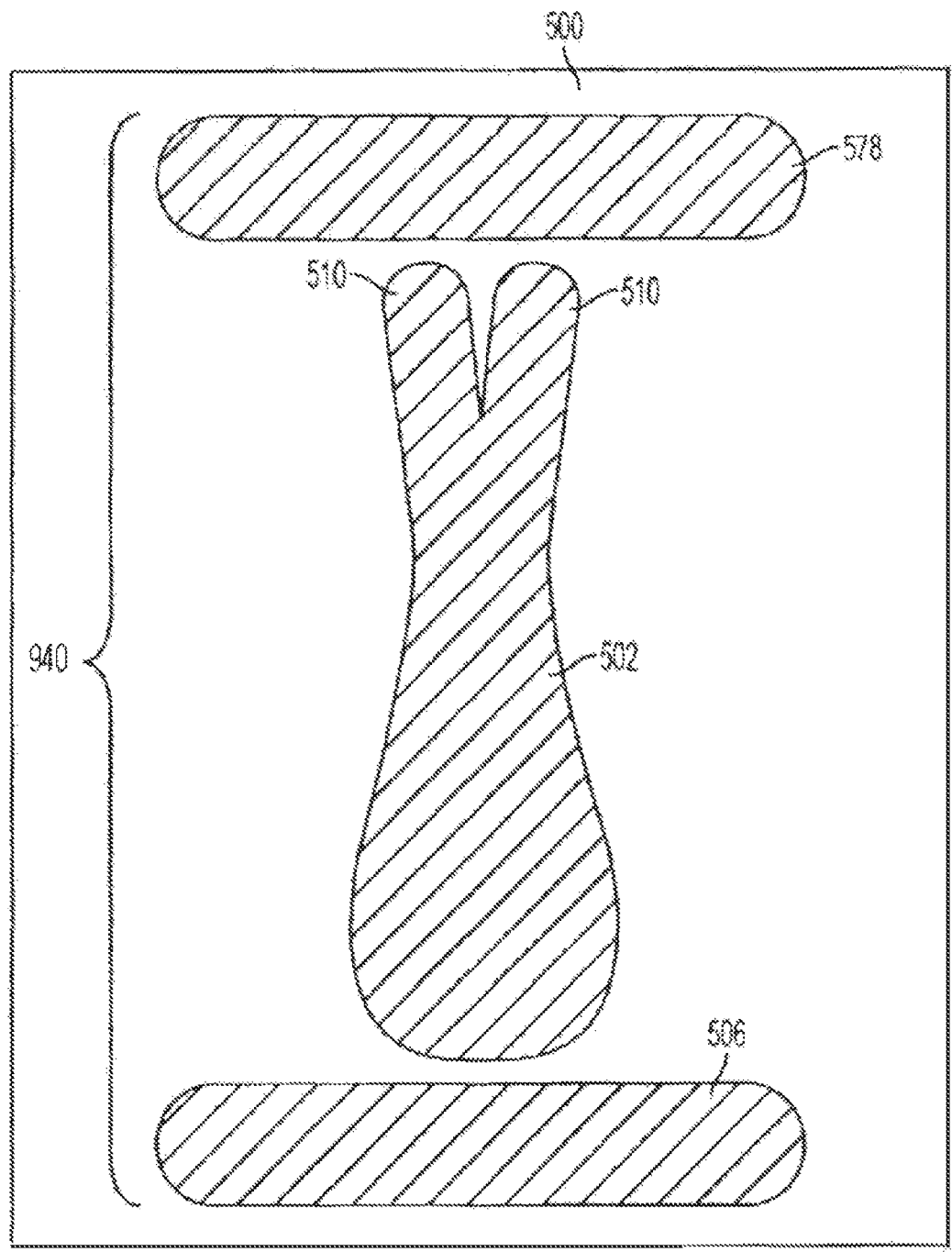
FIG. 20 illustrates a top view of a sheet of material containing a support system in accordance with an embodiment of the present invention.

Alternatively, as shown in FIG. 20, the support system 940 may include separate portions that can be removed from the sheet 500. The support system 940 includes the sole portion 502 with heel tabs 510, the ball strap 506, and the arch strap 578, each of which can be removed separately from the sheet 500 for application to the foot 540. For example, the user may apply the sole portion 502 first, and then apply either or both of the ball strap 506 and the arch strap 578 as the user sees fit. Alternatively, the user may only apply one of the sole portion 502, the ball strap 506 or the arch strap 578, or any combination thereof. Thus, the embodiment of FIG. 20 offers the user more flexibility in tailoring the treatment to the user's specific needs for treating pain while limiting the visibility of the support system 940.

Figure 21:
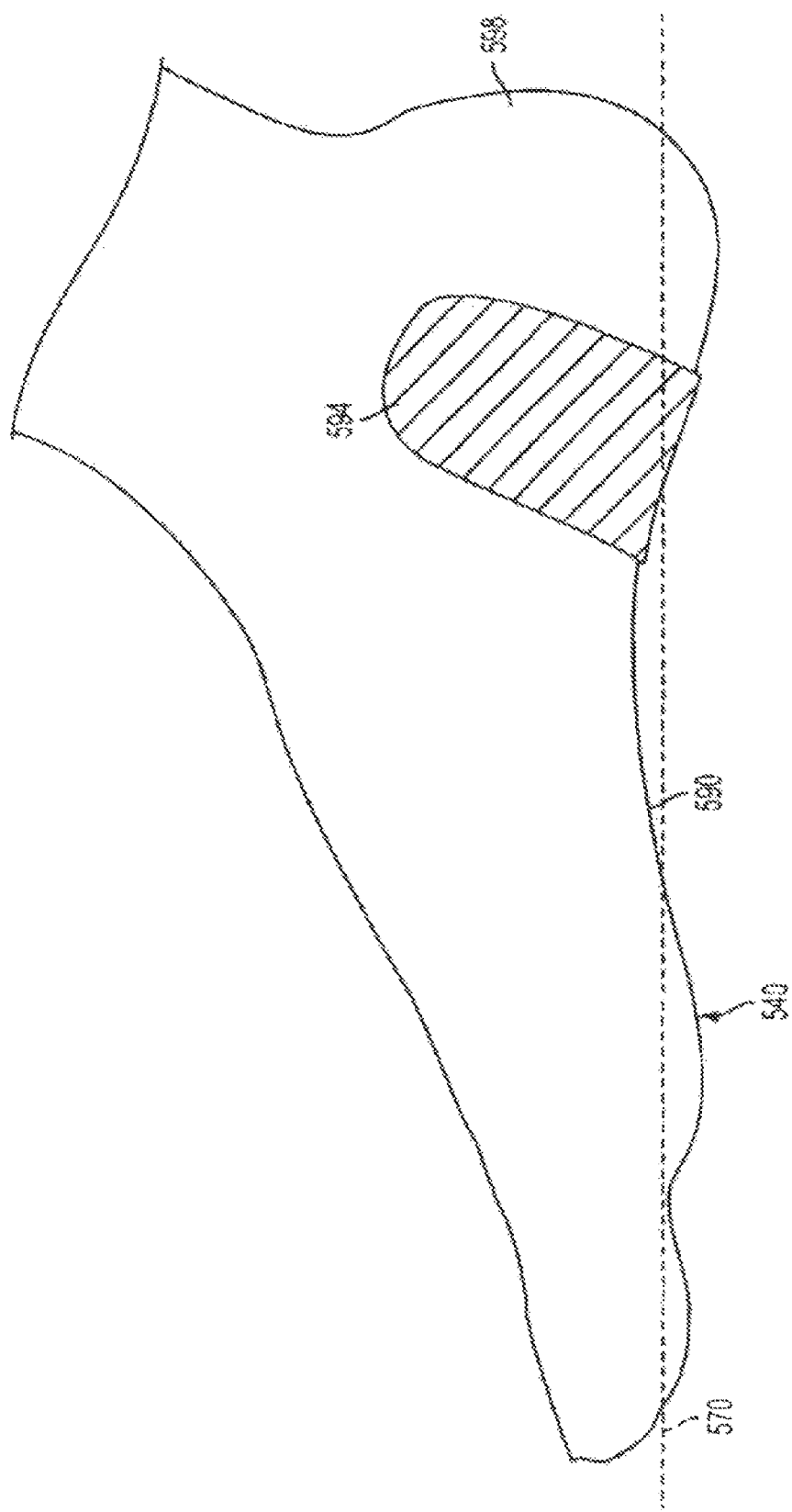
FIG. 21 illustrates a left side view of a foot and a strap affixed to the foot in accordance with an embodiment of the present invention.
Figure 22:
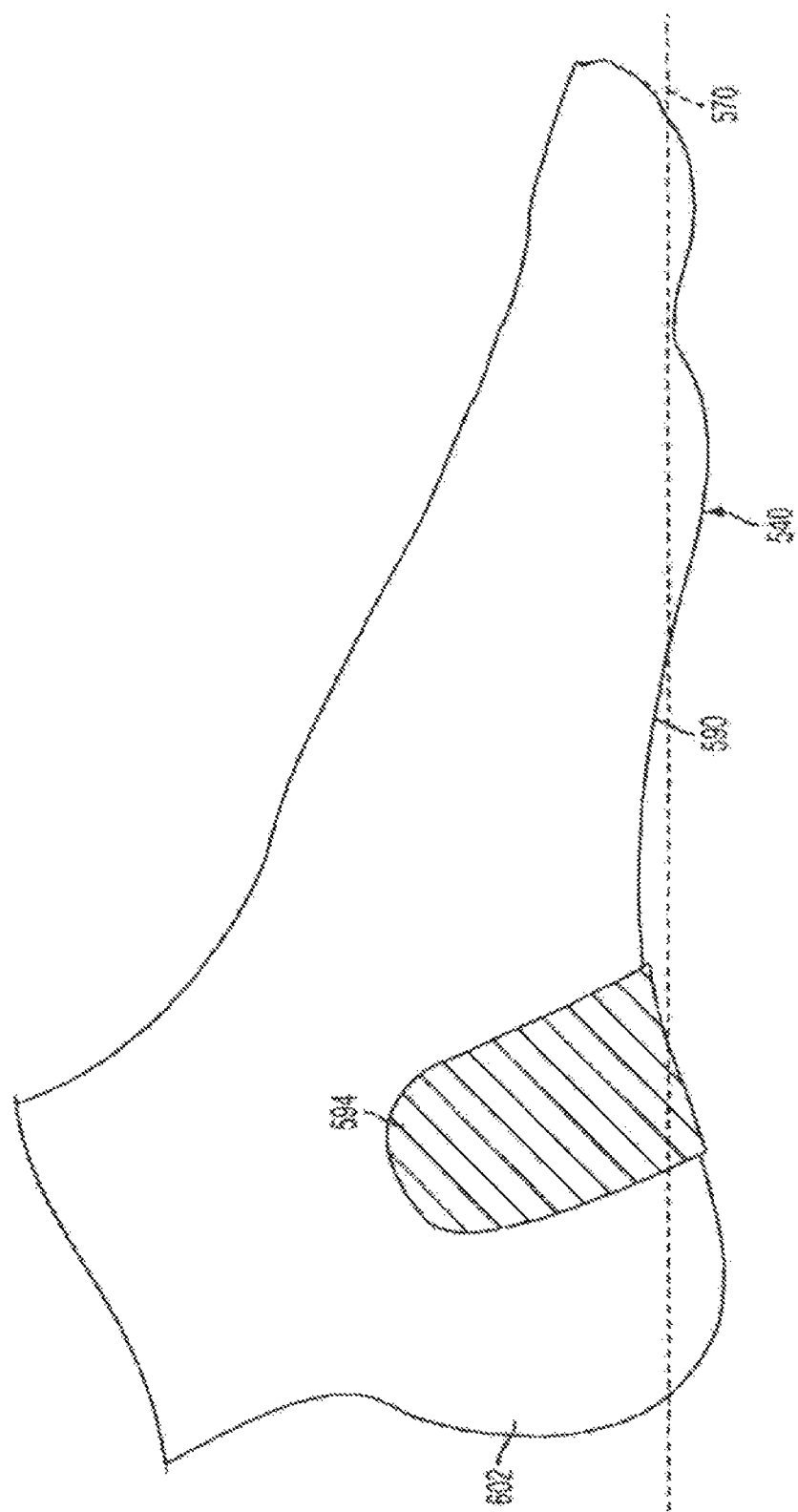
FIG. 22 illustrates a right side view of the foot and strap of FIG. 21.
Figure 23:
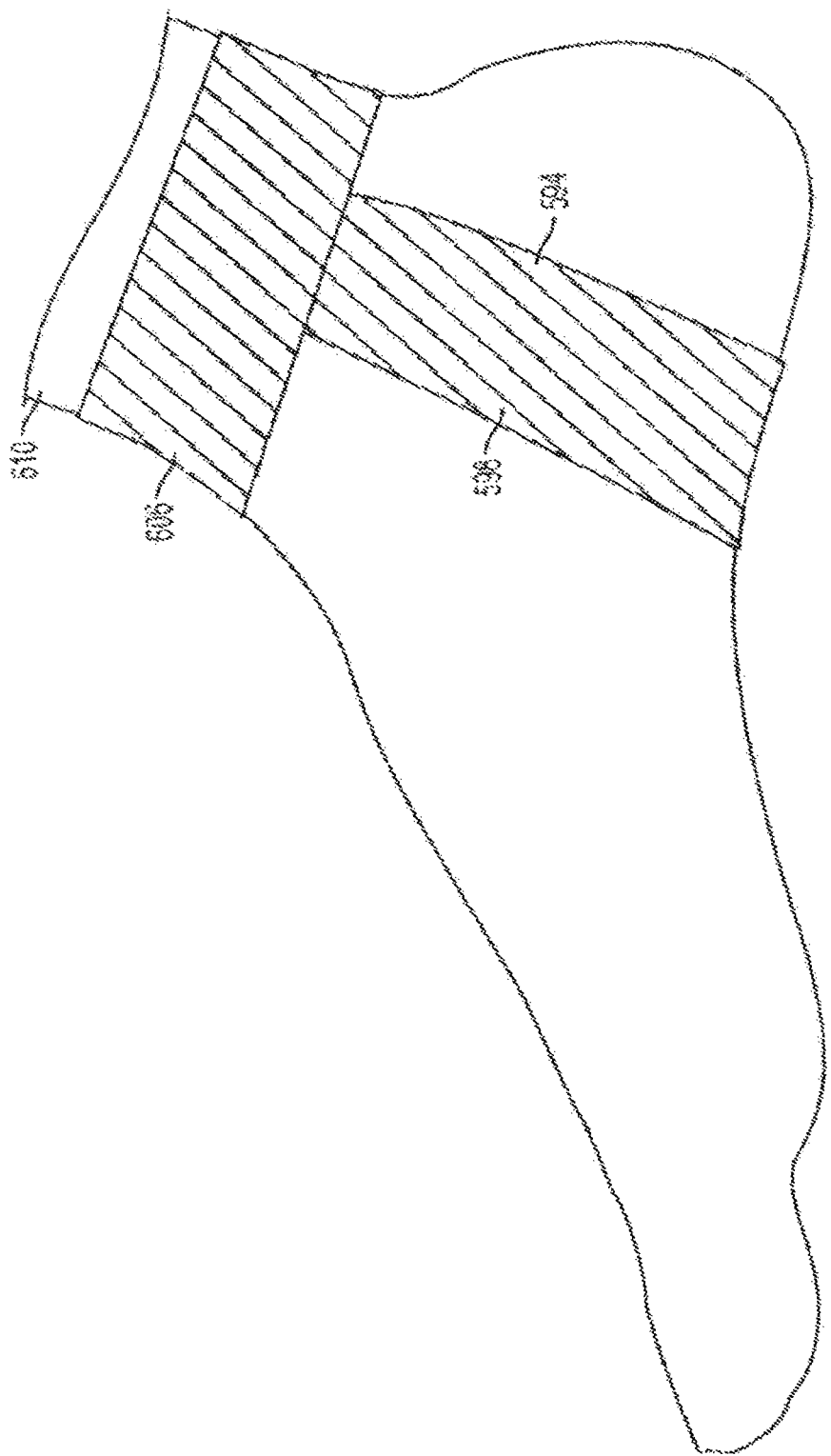
FIG. 23 illustrates a side view of a foot and a strap affixed to the foot in accordance with an embodiment of the present invention.

Alternatively, the support system may include a single strap that the user can use in combination with orthotic practices to address specific pain problems. The strap may be sized and shaped to address the particular areas of the user's foot that need treatment. FIGS. 21 and 22 illustrate opposite side views of a strap 594 applied to a foot 540. The single strap 594 may be applied to the foot 540 transversely to the arch 590 and longitudinal axis 570 of the foot 540 from ankle 598 to ankle 602. The strap 594 provides constant pressure along the arch 590 of the foot 540 to reduce inflammation and thus reduces pain. The strap 594 may be worn at night when the user sleeps. Alternatively, as shown in FIG. 23, the strap 594 may include a support strap 606 configured to hold the strap 594 about the ankles 598 and 602. By way of example only, the support strap 606 may be retained about the leg 610 by adhesive, elastic, or Velcro.

Figure 24:
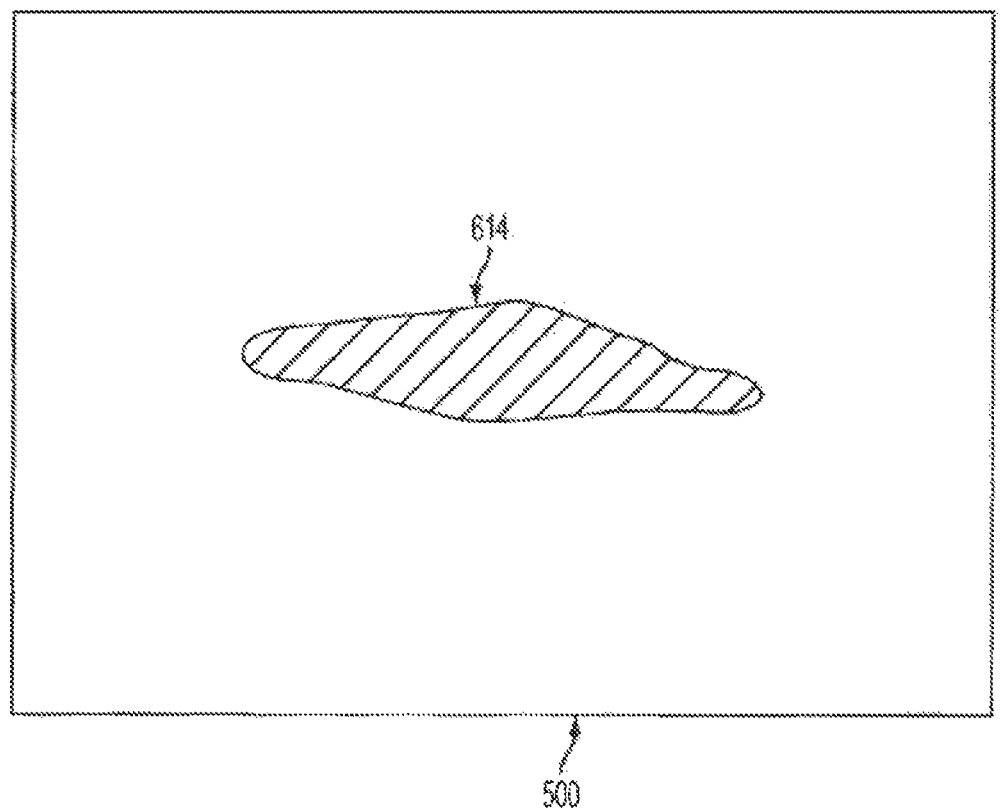
FIG. 24 illustrates a top view of a sheet of material containing a support system in accordance with an embodiment of the present invention.
Figure 25:
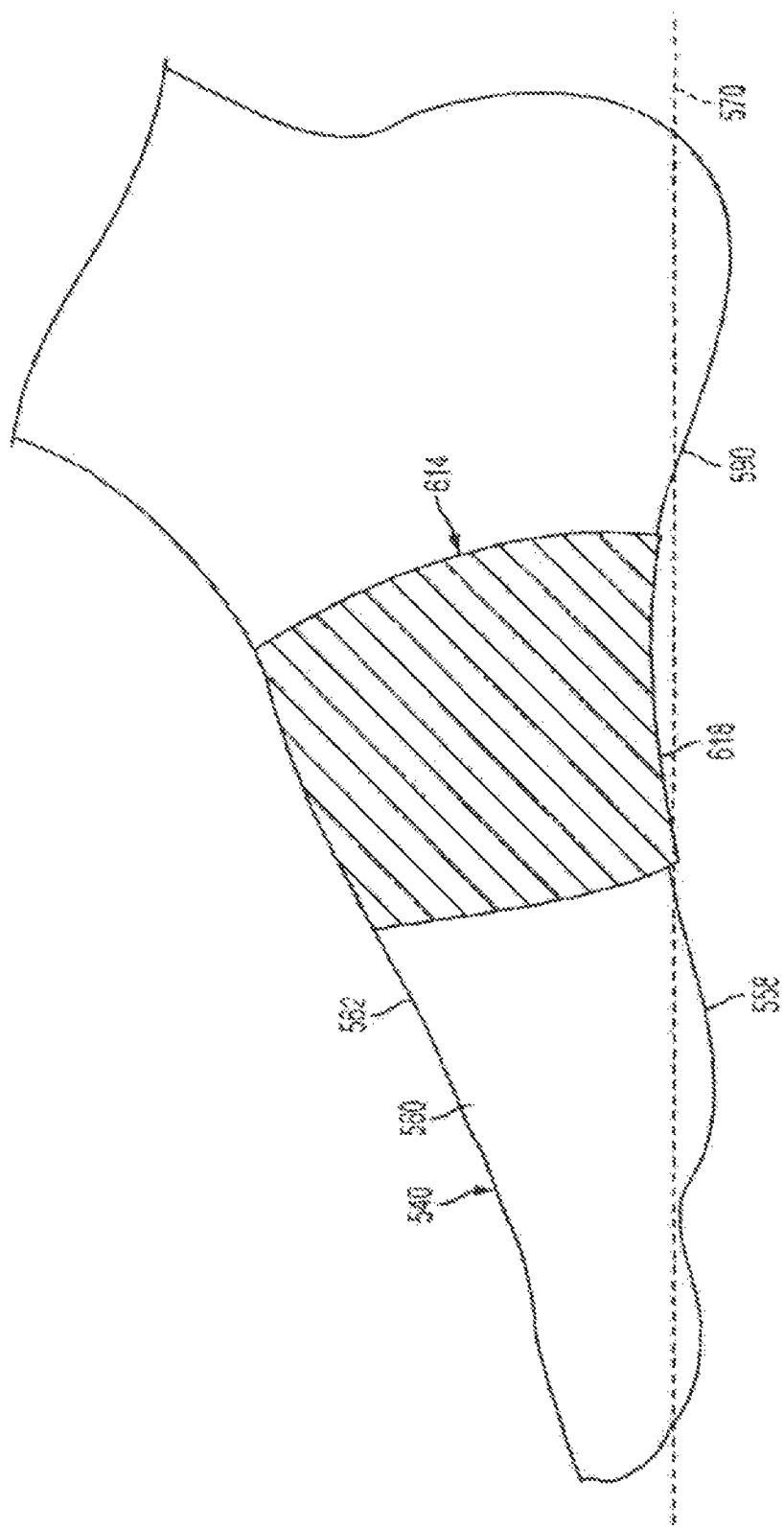
FIG. 25 illustrates a side view of a foot and the support system of FIG. 24.

FIG. 24 illustrates a top view of a diamond-shaped strap 614 that may be provided on a sheet 500 as part of a support system according to an embodiment of the present invention. As shown in FIG. 25, the strap 614 may be applied to the foot 540 transversely to the longitudinal axis 570 and arch 590 of the foot 540 across the sole 558 of the foot 540 and about the sides 560 and top 562 of the user's foot 540 like the arch strap 578 of FIG. 15. The strap 614 anatomically supports the medial arch of the foot 540 instead of specifically to the longitudinal arch.

Figure 26:
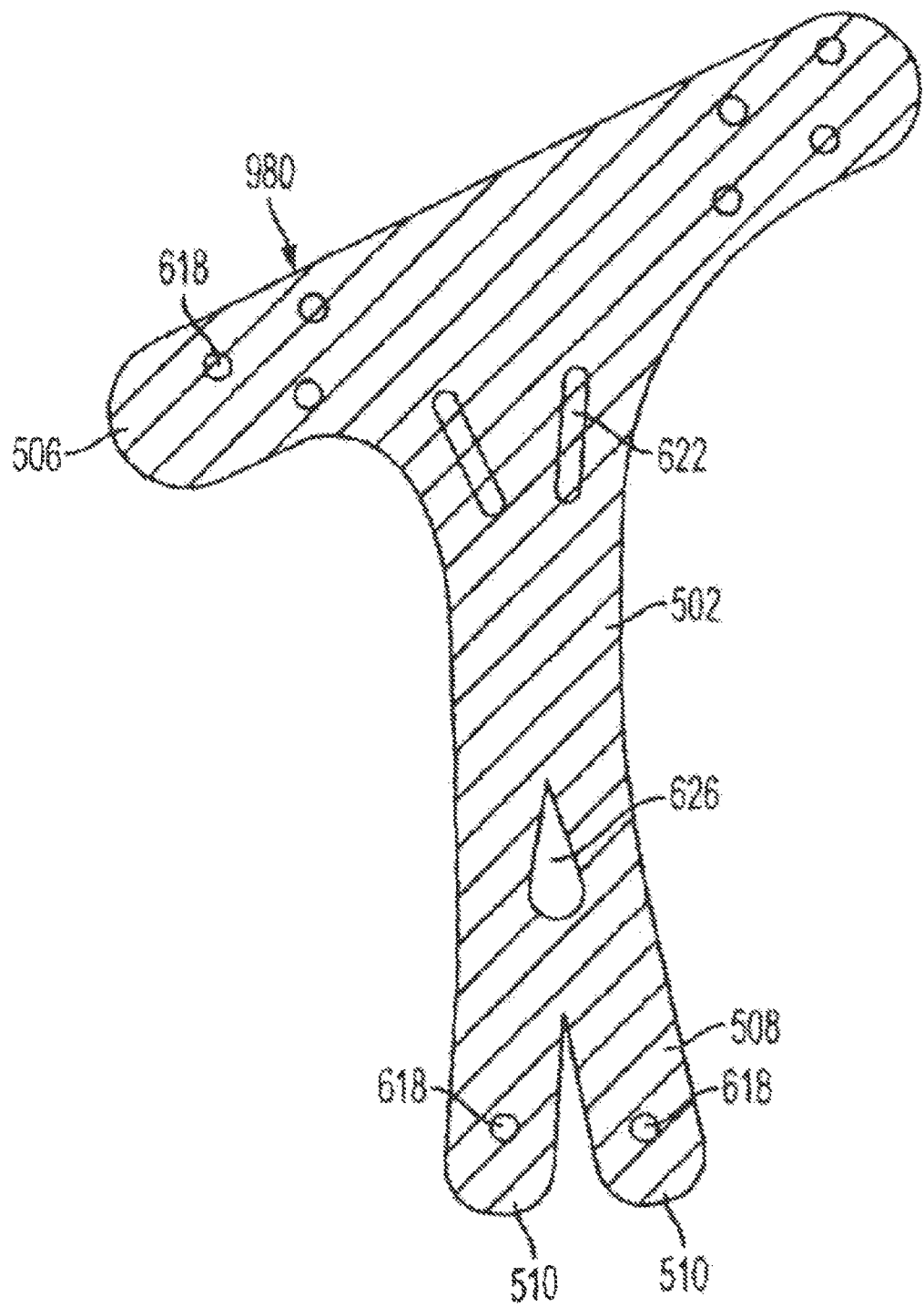
FIG. 26 illustrates a top view of a support system in accordance with an embodiment of the present invention.

FIG. 26 illustrates a top view of the support system 980 in accordance with an embodiment of the present invention. The support system 504 includes holes 618 along the ball strap 506 and heel tabs 510 and slots 622 and a tear-shaped aperture 626 along the sole portion 502. Alternatively, the support system 980 may include any number of apertures having other shapes. Alternatively, the support system 504 may have at least one of, or any combination of, the holes 618, slots 622 and aperture 626 at any other locations thereon. The holes 618, slots 622, and aperture 626 are provided to alter the stretch resistant properties of the support system 980, focus or transfer the stress carried by the support system 980, or aid in preventing direct application of pressure to inflamed areas of the foot when the support layer 508 of the support system 980 is applied to the user's foot. Also, the holes 618, slots 622, and aperture 626 allow the skin from the foot to breathe and allow the skin to contact surfaces in order to reduce the possibility of the user slipping while wearing the support system 980. Additionally, the holes 618, slots 622, and aperture 6226, may be ornamental. The holes 618, slots 622, and aperture 626 may be pre-cut into the support system 980 or may be created by the user.

Like the support system 400 of FIG. 3, the foot support kit serves to restrict extension of the tissue on the bottom of the foot and thus the level of tensile stress on the plantar fascia to reduce foot pain, arch pain, and heel pain, and to rehabilitate the plantar fascia, and to prevent injury to the plantar fascia. The stretch resistant properties of the support layer 508 share the stresses normally absorbed by the plantar fascia alone. The support layer 508 manages foot pain and addresses the cause of plantar fasciitis by controlling and limiting the stress on the plantar fascia and surrounding tissues across both the medial and longitudinal arches and thus minimizes tears in the plantar fascia.

The stretch resistant plantar fascia support system of the different embodiments may be used while sleeping, while walking around with barefeet, or while wearing various types of footwear. Also, the stretch resistant plantar fascia support system non-invasively reduces the level of tensile stress carried by the plantar fascia and may prevent the need for complex and expensive surgery.

For example, a consumer may wake-up in the morning and experience pain along the bottom of the consumer's foot. The consumer may recognize the pain as plantar fasciitis and desire to treat the pain. Rather than schedule an appointment with a doctor and have to travel to the doctor's office for treatment, during which time the plantar fascia may be subjected to further excessive tensile stress, the consumer may desire to treat the pain at home.

With the stretch resistant plantar fascia support system of the present invention, the consumer may save the time, expense, and pain of traveling to a doctor's office for treatment. To use the stretch resistant plantar fascia support system, the consumer would simply remove the removable protective covers that protect the adhesive layer and apply the stretch resistant plantar fascia support system to the affected area.

While the above scenario described the consumer applying the stretch resistant plantar fascia support after waking up in the morning, the stretch resistant plantar fascia support system may also be worn to bed at night. By wearing the stretch resistant plantar fascia support system to bed at night, the stretch resistant plantar fascia support system may aid in the healing process while the consumer sleeps and protects the plantar fascia during the first few steps in the morning when stress is re-applied.

In addition, the stretch resistant plantar fascia support system may be comfortably worn when the consumer is not currently experiencing pain, but anticipates the potential for injury during a strenuous activity. For example, a consumer with a history of frequent occurrences of plantar fasciitis may desire to return to a strict exercise regimen following a prolonged period of inactivity. To avoid overstressing the plantar fascia until the foot has had enough time to become re-accustomed to the stresses of exercise, the consumer may desire to use the easily applied stretch resistant plantar fascia support system rather than some of the more cumbersome, less effective, and inconvenient alternatives such as taping and molded arch supports.

To aid the consumer with installation of the stretch resistant plantar fascia support system, the removable protective covers, or other portions of the stretch resistant plantar fascia support system, may include numerical indicia that indicate the order in which portions of the stretch resistant plantar fascia support system are applied to the foot. The consumer then applies the stretch resistant plantar fascia support system to the consumer's foot in the prescribed order.

In addition, the stretch resistant plantar fascia support system is comfortable and form fitting. The stretch resistant plantar fascia support system may be supplied for a plurality of foot sizes and the consumer may select the stretch resistant plantar fascia support system much like shoes are selected based upon standard shoe sizes. The foot sole support of the stretch resistant plantar fascia support system may even be shaped to conform to the shape of the sole of a foot. If an adjustment is needed to adapt the stretch resistant plantar fascia support system to an irregularity in a particular consumer's foot, the stretch resistant plantar fascia support system may be easily adapted by cutting the stretch resistant plantar fascia support system to accommodate the irregularity.

Because the stretch resistant plantar fascia support system is form fitting, the consumer may wear the stretch resistant plantar fascia support system in a variety of situations. For example, if a woven rayon microfiber with a 3600 thread count and/or thickness less than 30 mils, or alternatively less than 15 mils, is used, then the stretch resistant plantar fascia support system is thin enough to comply with contours of the foot and strong enough to provide adequate strength. While the consumer has the stretch resistant plantar fascia support system attached to the consumer's foot, the consumer has the option of walking around in bare feet, pulling a sock over the foot, or putting on shoes. The consumer may also wear the stretch resistant plantar fascia support system while using other additional devices such as arch supports, night splints, and custom orthotics.

Also, the stretch resistant plantar fascia support system does not interfere with rotation and movement of the ankle or calves. The stretch resistant plantar fascia support system is positioned beneath the ankle. The heel straps and the heel strap tabs are sized to avoid interference with the ankle bone. Because the stretch resistant plantar fascia support system is positioned beneath the ankle, contact between adhesive and leg hair is reduced. Thus, the need for shaving portions of the leg and ankle is reduced.

Also, different embodiments of the stretch resistant plantar fascia support system may be used depending on the type of footwear the consumer desires to wear while the stretch resistant plantar fascia support system is attached. For example, if the consumer is going to wear sandals, the consumer may desire to use a stretch resistant plantar fascia support system with a foot sole support and no adhesive straps or tabs to reduce the visibility of the stretch resistant plantar fascia support system. On the other hand, the consumer may desire to wear boots, where visibility of the stretch resistant plantar fascia support system is not an issue, and the consumer desires to have straps and tabs along with the foot sole portion for added stability.

The present invention may also include other items that can benefit a user. For example, to minimize the potential for skin damage and foot odor from the presence of moisture, the stretch resistant plantar fascia support system may be made of a permeable material. The stretch resistant plantar fascia support system may be made of a permeable material that wicks moisture away from the skin or the stretch resistant plantar fascia support system may include holes in the material to allow for the evaporation of moisture. In conjunction with the permeable material, adhesive may be applied in an intermittent manner to further increase the permeability and reduce the presence of moisture trapped between the foot and the stretch resistant plantar fascia support system. Also, the stretch resistant plantar fascia support system may include additives such as medicines, anti-fungal treatments, anti-microbial treatments, anti-inflammatory treatments, cooling compounds, heating compounds, deodorants, zeolite, perfumes, moisturizers, tee tree oil, talcum powder, and zinc oxide.

Thus, the present invention provides an effective system for the treatment of plantar fasciitis that is both economical and easy to use. The present invention provides a stretch resistant system that may be discretely attached to a patient's foot and reduces stress on the plantar fascia.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A therapeutic article of manufacture suitable for adhesive application to a skin of a user, the article of manufacture comprising:
    an elongate support layer formed of a single layer of woven fabric having a ratio of elongation in percent to tensile strength (lb/in-width) that is less than 0.9 in only one of two test directions, wherein elongation, tensile strength, and test directions are determined under test conditions specified in ASTM (American Society for Testing and Materials) D3759;
    an adhesive intermittent across the elongate support layer; and
    a removable cover layer releasably retained on the adhesive.

2. The article of manufacture of claim 1, wherein the elongate support layer exhibits less than 15% elongation when subjected to a 25 lb tensile load under test conditions specified in ASTM (American Society for Testing and Materials) D3759 in only one of the two test directions.

3. The article of manufacture of claim 1, wherein the elongate support layer has a thickness that is less than 30 mils, and wherein the elongate support layer is permeable allowing moisture transfer.

4. The article of manufacture of claim 1, wherein:
    the elongate support layer and the adhesive form a support device; and
    at least one support device is packaged for an individual application.

5. The article of manufacture of claim 1, wherein:
    the elongate support layer and the adhesive form a support device;
    the article of manufacture further includes multiples of separated support devices formed in a continuous roll.

6. The article of manufacture of claim 5, wherein the woven fabric is a microfiber fabric.

7. The article of manufacture of claim 1, wherein the woven fabric is a microfiber fabric.

8. An article of manufacture suitable for use on a skin of a human user, the article of manufacture comprising:
    a support layer formed of a single layer of woven material having a ratio of elongation in percent to tensile strength (lb/in-width) that is less than 0.9 in only one of two test directions, wherein elongation, tensile strength, and test directions are determined under test conditions specified in ASTM (American Society for Testing and Materials) D3759,
    wherein:
        the support layer exhibits less than 15% elongation when subjected to a 25 lb tensile load under test conditions specified in ASTM D3759 in only one of the two test directions; and
        the support layer has a thickness that is less than 30 mils;
    an adhesive intermittent across the support layer; and
    a removable cover layer releasably retained on the adhesive.

9. The article of manufacture of claim 8, wherein:
    the support layer and the adhesive form a support device; and
    the article of manufacture further includes a package containing multiples of separate support devices formed in a continuous roll.

10. The article of manufacture of claim 9, wherein the woven material is a microfiber fabric.

11. The article of manufacture of claim 8, wherein:
the support layer and the adhesive form a support device;
the support device is cut from the support layer and is shaped for interchangeable use on either a left or right foot.

12. The article of manufacture of claim 8, wherein the woven material is a woven microfiber.

* * * * *